(12) United States Patent
Glass et al.

(10) Patent No.: US 7,977,120 B2
(45) Date of Patent: Jul. 12, 2011

(54) FLUORESCENT SENSORS FOR CELLULAR AMINES

(75) Inventors: Timothy Glass, Columbia, MO (US); Kristen Secor, Cary, NC (US)

(73) Assignee: The Curators of the University of Missouri, Columbia, MO (US)

( * ) Notice: Subject to any disclaimer, the term of this patent is extended or adjusted under 35 U.S.C. 154(b) by 275 days.

(21) Appl. No.: 11/996,878

(22) PCT Filed: Jul. 28, 2006

(86) PCT No.: PCT/US2006/029760
§ 371 (c)(1),
(2), (4) Date: Jul. 25, 2008

(87) PCT Pub. No.: WO2007/016495
PCT Pub. Date: Feb. 8, 2007

(65) Prior Publication Data
US 2009/0011454 A1    Jan. 8, 2009

Related U.S. Application Data

(60) Provisional application No. 60/704,012, filed on Jul. 29, 2005, provisional application No. 60/735,695, filed on Nov. 10, 2005.

(51) Int. Cl.
*G01N 33/53*    (2006.01)

(52) U.S. Cl. ........................................................ 436/800
(58) Field of Classification Search ................... 435/800
See application file for complete search history.

(56) References Cited

FOREIGN PATENT DOCUMENTS
WO  WO-2007016495  A2  2/2007
WO  WO-2007016495  A3  2/2007

OTHER PUBLICATIONS

Feuster, E., et al., "Detection of Amines and Unprotected Amino Acids in Aqueous conditions by Formation of Highly Fluorescent Iminium Ions", *J. Am. Chem. Soc.*, 125, (2003),17174-16175.
Secor, K., et al., "Fluorescent sensors for diamines", *Journal of Materials Chemistry*,15(37), (2005),4073-4077.
Secor, K., et al., "Selective Amine Recognition Development of a Chemosensor for Dopamine and Norepinephrine", *Department of Chemistry*, 6(21), (2004),3727-3730.

*Primary Examiner* — Sue Liu
*Assistant Examiner* — Bin Shen
(74) *Attorney, Agent, or Firm* — Thomas Coburn LLP

(57) ABSTRACT

The invention provides compounds of formulas I, II, and III, methods of making them, and methods of their use. The compounds of the invention can be used as fluorescent sensors, for example, to detect an amine-containing analyte in a biological sample. The compounds can be selective for one type of amine over others and the amount of fluorescence can be correlated with the concentration of the amine in the sample.

12 Claims, 8 Drawing Sheets

Scheme 2

Scheme 3

Scheme 4

Scheme 5

FLUORESCENT SENSORS FOR CELLULAR AMINES

RELATED APPLICATIONS

This application is a U.S. National Stage Filing under 35 U.S.C. 371 from International Application Number PCT/US2006/029760, filed Jul. 28, 2006 and published in English as WO 2007/016495 on Feb. 8, 2007, which claims priority under 35 U.S.C. §119(e) to U.S. Provisional Application Ser. No. 60/704,012, filed Jul. 29, 2005, and U.S. Provisional Application Ser. No. 60/735,695, filed Nov. 10, 2005, which applications and publication are incorporated herein by reference.

GOVERNMENT SUPPORT

This invention was made in part from government support under Grant No. GM059245 from the National Institutes of Health. The U.S. Government has certain rights in the invention.

FIELD OF THE INVENTION

The present invention relates to fluorescent sensors for intracellular analyte detection. More particularly, the present invention relates to fluorescent sensors for selectively sensing amine-containing analytes.

BACKGROUND OF THE INVENTION

Detection of Organic Compounds in Biological Systems

Fluorescent probes have been useful in elucidating biochemical mechanisms and processes inside of living cells via fluorescent microscopy. The technique is particularly valuable because it can be non-destructive to a living cell and the sensors can be observed in real time over the course of cellular events.

Fluorescent probes fall into two main classes, chemosensors and biosensors, and both have advantages and disadvantages when applied to a biological system. Biosensors are fluorescently labeled proteins, most often antibodies. These types of sensors can be generated with specificity for any macromolecule against which an antibody can be raised, but generally with poor cell permeability. Chemosensors are typically synthetic compounds and used in cells mainly to quantify the concentration of certain inorganic ions, such as, $Na^+$, $K^+$, $Ca^{+2}$, $Mg^{+2}$, $Zn^{+2}$, and $Cl^-$. Despite significant advances in molecular recognition and chemical sensing, chemosensors have enjoyed only limited success in practical intracellular applications for sensing cellular conditions such as pH and $pO_2$ and analytes beyond those mentioned above.

Very few intracellular fluorescent sensors have been developed for detection of small organic compounds in a biological system. Because small organic compounds are not easily targeted by antibodies, the corresponding biosensors are not available. Existing chemosensors for organic analytes are not yet useful in a practical sense.

Requirements for Intracellular Fluorescent Sensors:

To be useful in a cellular assay, a sensor must have good cell permeability and optical properties. A good sensor must be excited at or above 450 nm. Excitation wavelengths below this threshold can damage the cell and cause interference from cell autofluorescence. For static measurements in cells, a ratiometric sensor is often preferred because it is self-calibrated and easy to use. For specific application to neurochemistry, speed is often important. In this instance, an 'on/off' sensor may be better suited due to its rapid measurement.

Despite the strict fluorescence requirements, a major challenge still lies in obtaining specific, high affinity recognition of organic analytes in physiological conditions. A successful sensor must bind the analyte with a dissociation constant in the same range as the concentration at which the analyte is present in solution. Meeting this requirement ensures that the sensor can adequately sense increases and decreases in the concentration of the analyte. Unfortunately, a large portion of the state-of-the-art molecular recognition of organic compounds is still being performed in non-aqueous or partly aqueous solution, often using hydrogen bonding as a driving force.

In a purely aqueous environment, strong intermolecular hydrogen bonds are rare. Typically, for aqueous phase recognition ion-ion interactions, metal chelation, or covalent bonding (e.g., boronate ester formation) are utilized to provide the driving force for association. It is difficult to overemphasize how weak some of these interactions become in the high-salt buffer conditions that are necessary for cellular work. Ion-ion interactions, for example, are significantly decreased when buffer concentration rises. Metal-ligand interactions are not affected as much by ionic strength, thus sensors for metal ions are the most common practically useful probes available.

Finally, a practical chemosensor must also be selective, giving signal only in the presence of the specified analyte. An inability to meet this criterion is almost certainly the main failing of most current approaches to chemosensors given the complexity of the cellular milieu. This problem can be somewhat alleviated by judicious choice of target, but ultimately, needs to be addressed.

Current Methods in Mapping and Visualizing Movement of Neurotransmitters:

The study of synaptic transmission is a difficult and tremendously important area of research. It would be beneficial to be able to map the movement of neurotransmitters and neuromodulators in and around neurons in order to study their functions and mechanisms of action. It is also important to measure these species in real time because of their fast, quantized release and rapid re-uptake/diffusion out of the synapse. The biological community has invested significant resources in the development of indirect experiments to visualize synaptic vesicles and their contents. A convenient fluorescent sensor (in this case, a chemosensor) for neurotransmitters in neurons would make direct visualization and mapping possible. However, such a sensor is currently unavailable.

The biology of the synapse is quite complicated. Neurotransmitters are packaged into vesicle at very high concentrations, ranging from 500 mM for glutamate to approximately 1M for catecholamines. As these are secretory vesicles, the neurotransmitters are stored at low pH (about 5.0-5.5). Vesicles traffic to the synapse where a few of them dock to specialized areas of the membrane in preparation for release. Upon the appropriate signal, some of the docked vesicles fuse with the membrane and exocytose their contents into the synapse. This is the synaptic release event.

During a basic release event, the vesicles may completely fuse with the cell membrane and lose their identity, or they may be retrieved from the membrane and immediately reform as a vesicle. Upon retrieval, vesicles are reloaded with neurotransmitter and protons (to re-establish the pH gradient). Because of the high concentration of neurotransmitter in the vesicle, the concentration of neurotransmitter in the synapse rises rapidly from 1M concentrations to low mM concentrations upon vesicle exocytosis. Concentrations of neurotransmitter quickly fall following the release event due to reuptake, degradation, and diffusion of the neurotransmitter out of the synapse. In addition, a variety of neuromodulatory compounds and ions may also modify levels of protein expression and alter synaptic transmission. All of these events need to be studied in live, functioning cells. In this regard, fluorescent chemical sensors can potentially provide an ideal tool for the study of synaptic function.

Currently, the synaptic events can be studied by fluorescent microscopy using several existing chemosensors, but with significant limitations. Existing chemosensors include $Ca^{+2}$ and $Zn^{+2}$ sensors (for example, compound 1, FIG. 1) because these ions have been established as neuromodulators. Certain weakly basic probes that accumulate only in the low pH environment of the vesicles, such as compound 2 (FIG. 1) can be used to visualize the vesicles themselves, however, compound 2 labels all acidic compartments regardless of the contents.

"FM" dyes (e.g., compound 3, FIG. 1), another type of chemosensor, become fluorescent following partition into the cell membrane. By appropriate application and washing, the secretory vesicles can be labeled with the membrane dye and residual dye in the cell membrane can be removed. Upon fusion of the vesicle with the membrane, the marker diffuses into the cell membrane and the vesicle loses its label. It is difficult, however, to interpret the decrease in fluorescence because the dye is a complex marker of the membrane and not the vesicle cargo.

Additionally, some genetic tools can link green fluorescent protein with vesicle-associated proteins such that the vesicles are fluorescently labeled. However, using these tools requires genetic manipulation of tissue, which is sometimes not possible or at least significantly inconvenient. Moreover, attaching the rather large green fluorescent protein to vesicle cargo peptides may alter their packaging and release.

A non-fluorescent technique for detecting the release of catecholamines is microelectrode electrochemistry. Catecholamines (including dopamine) are an important class of neurotransmitters that are involved in a variety of central nervous system functions. Direct dopamine detection has been accomplished using electrochemical techniques due to the favorable redox properties of the catechol. However, competition with other oxidizable cell components (e.g., ascorbate) is problematic and spatial resolution is not possible. In contrast, glutamate can only be analyzed by a slow, destructive enzymatic assay not suitable for intracellular applications.

Malfunction of dopamine-responsive neurons has been implicated in a number of disease states including Parkinson's disease, sparking the development of tools to study these systems. The drug L-DOPA is used to treat Parkinson's disease and acts by increasing the amount of dopamine that is packaged in a vesicle. Antidepressant drugs such as fluoxetine (Prozac) act by blocking uptake of the monoamine neurotransmitter serotonin into neurons. Discovery of new drugs that affect neurotransmitter uptake into neurons or packaging could thus be greatly aided by chemical sensors for neurotransmitters that can be used with living neurons.

Accordingly, there is a need for a chemosensor that provides a signal only in the presence of one or more specific analytes. There is also a need for a series of fluorescence chemosensors to detect an organic primary-amine-containing analytes, such as, neurotransmitters and diamino-analytes, in a live cell.

SUMMARY OF THE INVENTION

The present invention provides a series of fluorescent sensors that are highly fluorescent, effective, and selective in detecting primary-amine-containing analytes. The analytes can be neurotransmitters or diamino-analytes in physiological conditions.

Accordingly, the invention provides a compound of formula I:

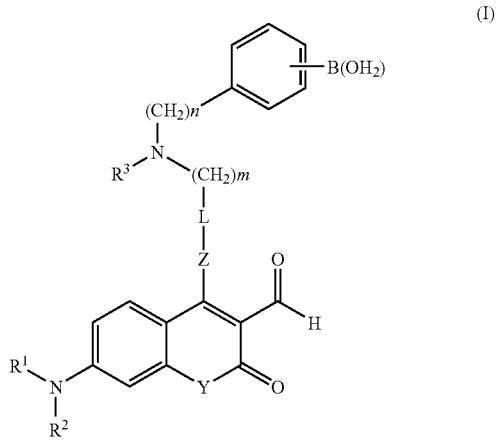

wherein
$R^1$, $R^2$ and $R^3$ are each independently hydrogen, alkyl, aryl, or cycloalkyl; or
$R^1$ and $R^2$ together with the nitrogen to which they are attached form a heterocycle with four to six atoms in the ring;
Y is O or N—R wherein R is hydrogen, alkyl, aryl, or cycloalkyl;
Z is —$CH_2$— or a direct bond;
L is O, S, Ph, or a direct bond;
m is 0 to about 6; and n is 1 to about 5.

The invention also provides a compound of formula III:

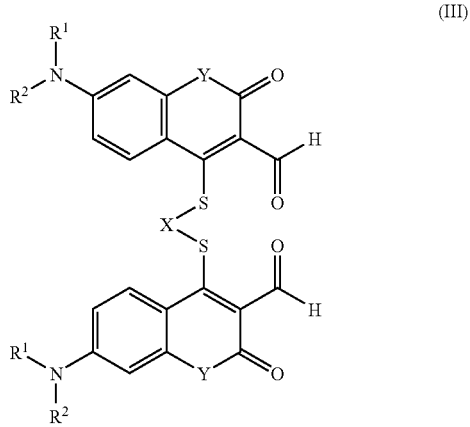

wherein
$R^1$ and $R^2$ are each independently hydrogen, alkyl, aryl, or cycloalkyl; or
$R^1$ and $R^2$ together with the nitrogen to which they are attached form a heterocycle with four to six atoms in the ring;
Y is O or N—R wherein R is hydrogen, alkyl, aryl, or cycloalkyl; and
X is alkyl, aryl, cycloalkyl, or alkyl interrupted by aryl.

The invention also provides a series of fluorescent sensors with a coumarin aldehyde core ("Coumarin-Based Sensors") having the formula I-1:

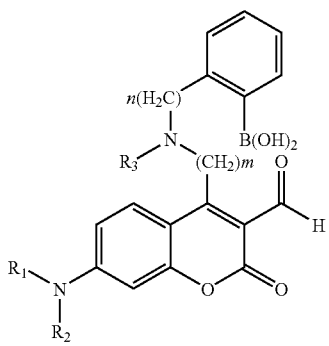

(I-1)

wherein $R_1$, $R_2$, and $R_3$ are each independently hydrogen, alkyl, alkylene, aryl, or cycloalkyl groups; m is 1-5, and n is 1-2.

The present invention further provides a series of fluorescent sensors with a quinolone aldehyde core ("Quinolone-Monomer Sensors") having the formula II-1:

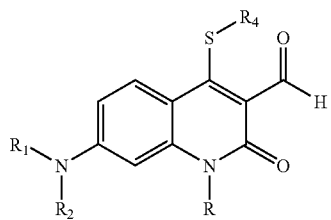

(II-1)

wherein R, $R_1$, $R_2$, and $R_4$ are each independently hydrogen, alkyl, alkylene, aryl, or cycloalkyl groups.

Furthermore, the present invention provides a series of Quinolone-Dimer Sensors having the formula III-1:

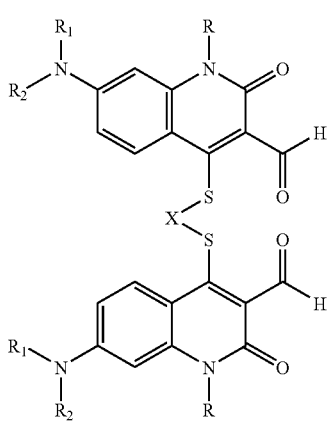

(III-1)

wherein R, $R_1$, and $R_2$ are each independently hydrogen, alkyl, alkylene, aryl, or cycloalkyl groups; and X is alkyl, alkenyl, alkynyl, aryl, or cycloalkyl.

The invention also provides a method of detecting an amine-containing analyte in a biological sample comprising contacting the biological sample with a compound described herein, and detecting the presence or absence of fluorescence in the sample, wherein the presence of fluorescence indicates the presence of an amine in the sample. The method can also include measuring the amount of fluorescence in the sample and correlating the amount of fluorescence in the sample with a concentration of the amine in the sample.

The present invention further provides a method of detecting cellular amines in a biological sample using aforesaid fluorescent sensing compounds, methods of making such compounds, and intermediates in the preparation of the compounds of the invention.

DETAILED DESCRIPTION OF THE INVENTION

Figure 1:
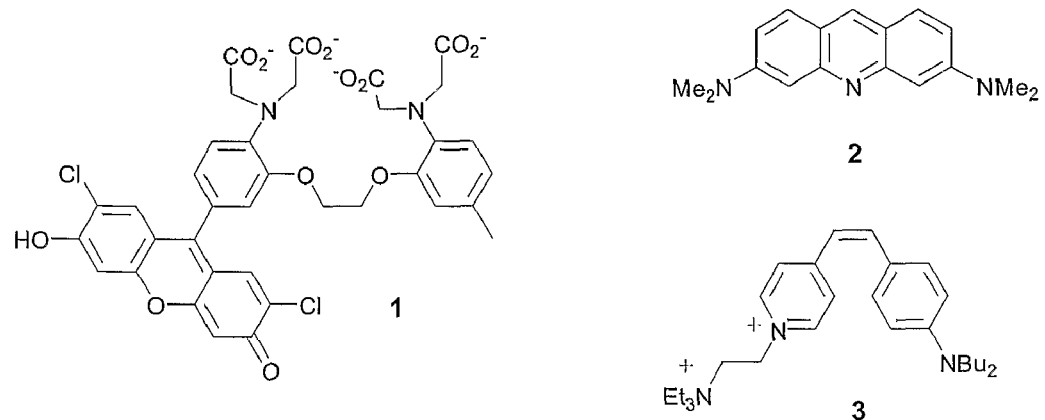
FIG. 1 illustrates chemical structures of representative fluorescent sensors currently used in neurobiology.

Unless otherwise defined, all technical and scientific terms used herein have the same meaning as commonly understood by one of ordinary skill in the art to which this invention belongs. Throughout the specification and claims, a given chemical formula or name shall encompass all optical and stereoisomers as well as racemic mixtures where such isomers and mixtures exist.

The invention provides a compound of formula I:

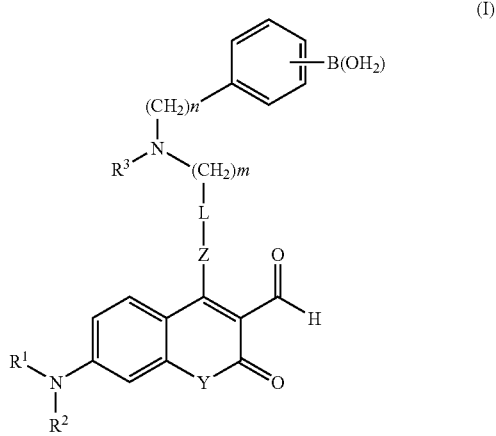

(I)

wherein

R[1], R[2], and R[3] are each independently hydrogen, alkyl, aryl, or cycloalkyl; or R[1] and R[2] together with the nitrogen to which they are attached form a heterocycle with four to six atoms in the ring;

Y is O or N—R wherein R is hydrogen, alkyl, aryl, or cycloalkyl;

Z is —CH$_2$— or a direct bond;

L is O, S, Ph, or a direct bond;

m is 0 to about 6; and n is 1 to about 5.

The compound of formula I can be a fluorescent sensor.

In one embodiment, R[1] and R[2] are both alkyl, for example, (C$_1$-C$_6$)alkyl. In another embodiment, R[1] and R[2] are both methyl or both ethyl.

In one embodiment, R[3] is alkyl. In another embodiment, R[3] is methyl.

In one embodiment, Y is O. In another embodiment, Y is N—R. R can be a variety of typical nitrogen substituents, including nitrogen protecting groups. R can be benzyl (a phenyl substituted alkyl). R can also be alkyl. The alkyl of R can be a (C$_5$-C$_{20}$)alkyl, wherein the alkyl chain is interrupted by 1-10 non-peroxide oxygen atoms. For example, the alkyl chain that is interrupted by 1-10 non-peroxide oxygen atoms can be a polyethoxy group, such as —CH$_2$CH$_2$OCH$_2$CH$_2$OCH$_3$.

In one embodiment, Z is —CH$_2$—. In another embodiment, Z is a direct bond.

In one embodiment, L is O. In another embodiment, L is S. In another embodiment, L is Ph (a phenyl diradical). In another embodiment, L is a direct bond.

In one embodiment, m is 1, 2, 3, 4, or 5. In other embodiments, m is 0.

In one embodiment, n is 1.

In one embodiment, the boronic acid group is in an ortho orientation.

In certain specific embodiments, the compound of formula I has the structure:

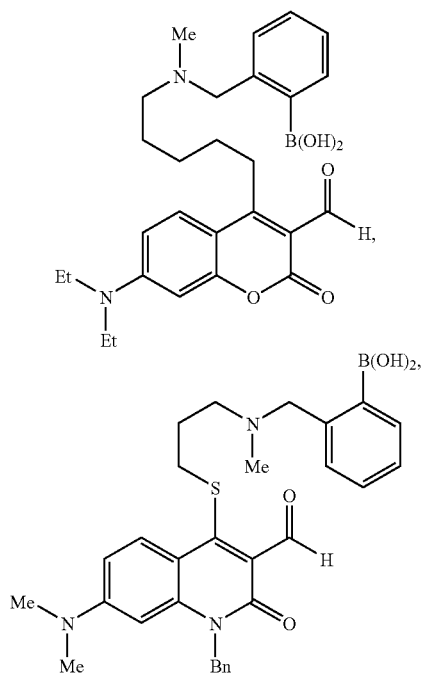

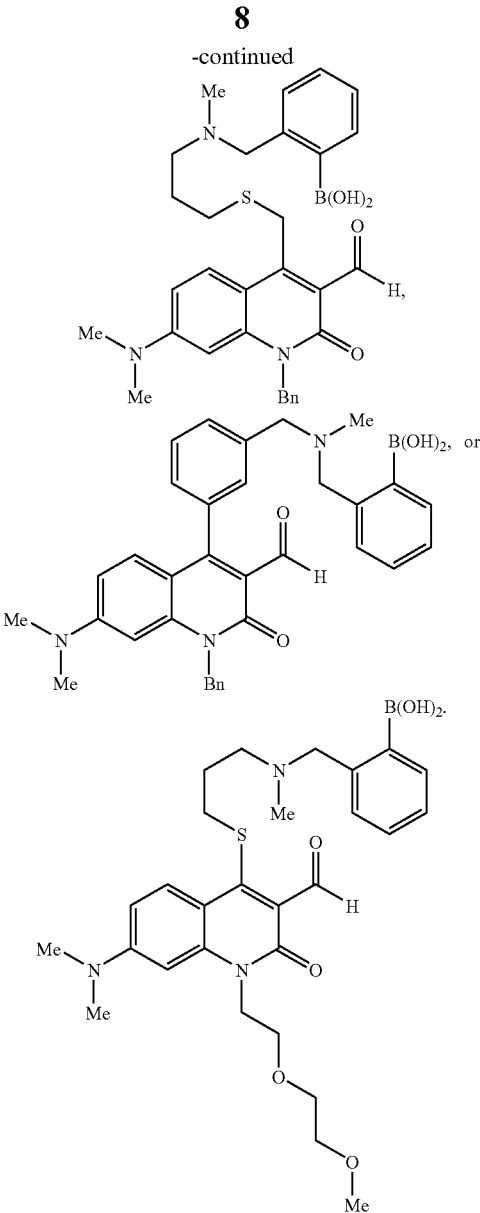

The invention also provides a compound of formula III:

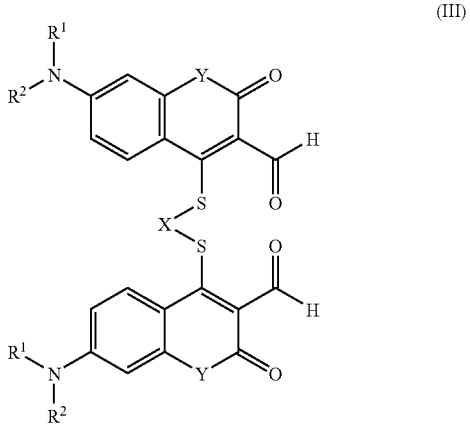

wherein

R$^1$ and R$^2$ are each independently hydrogen, alkyl, aryl, or cycloalkyl; or

R$^1$ and R$^2$ together with the nitrogen to which they are attached form a heterocycle with four to six atoms in the ring;

Y is O or N—R wherein R is hydrogen, alkyl, aryl, or cycloalkyl; and

X is alkyl, aryl, cycloalkyl, or alkyl interrupted by aryl.

The compound of formula III can be a fluorescent sensor.

In one embodiment, R$^1$ and R$^2$ are both alkyl. In another embodiment, each R$^1$ and R$^2$ are methyl. In yet another embodiment, each R$^1$ and R$^2$ are ethyl.

In one embodiment, Y is O. In another embodiment, Y is N—R. R can be a variety of typical nitrogen substituents, including nitrogen protecting groups. R can be benzyl (a phenyl substituted alkyl). R can also be alkyl. The alkyl of R can be a (C$_5$-C$_{20}$)alkyl, wherein the alkyl chain is interrupted by 1-10 non-peroxide oxygen atoms. For example, the alkyl chain that is interrupted by 1-10 non-peroxide oxygen atoms can be a polyethoxy group, such as —CH$_2$CH$_2$OCH$_2$CH$_2$OCH$_3$.

In one embodiment, X is alkyl (a diradical linking group). The alkyl can be a (C$_1$-C$_8$)alkyl. The alkyl can be optionally substituted, optionally branched, optionally unsaturated, or a combination thereof. In another embodiment, X is aryl. The aryl can be ortho or meta substituted aryl. In yet another embodiment, X is alkyl interrupted by aryl, for example, a phenyl diradical, such as —CH$_2$-Ph-CH$_2$—. The substitution of the phenyl group can be ortho, meta, or para.

The invention further provides a coumarin-based fluorescence sensing compound of Formula I-1:

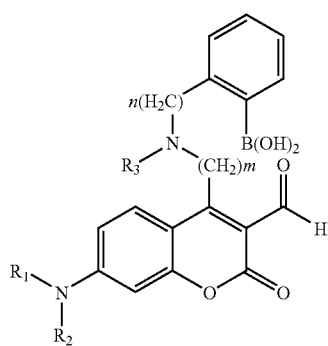

(I-1)

wherein R$_1$, R$_2$, and R$_3$ are each independently hydrogen, alkyl, alkylene, aryl, or cycloalkyl groups; m is 1-5, and n is 1-2. In one embodiment (Ia), R$_1$ and R$_2$ are ethyl; R$_3$ is methyl; m is 5 and n is 1.

The invention also provides a quinolone-monomer-based fluorescence sensing compound of Formula II-1:

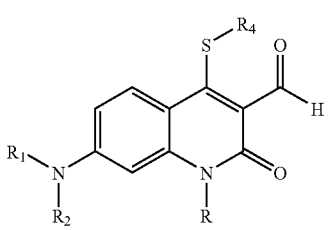

(II-1)

wherein R, R$_1$, R$_2$, and R$_4$ are each independently hydrogen, alkyl, alkylene, aryl, or cycloalkyl groups.

In one embodiment (IIa), R is benzyl; R$_1$ and R$_2$ are methyl; and R$_4$ is ethyl. In another embodiment (IIb), R is benzyl; R$_1$ and R$_2$ are both methyl; and R$_4$ is —N-propyl-N-methyl-ortho-aminomethyl phenylboronic acid (—(CH$_2$)$_3$N(CH$_3$) CH$_2$C$_6$H$_4$B(OH)$_2$).

The present invention further provides a quinolone-dimer-based fluorescence sensing compound of the Formula III-1:

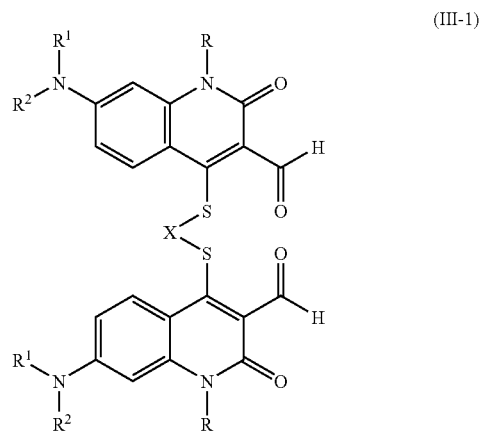

(III-1)

wherein R, R$_1$, and R$_2$ are each independently hydrogen, alkyl, alkylene, aryl, or cycloalkyl groups; and X is alkyl, alkenyl, alkynyl, aryl, or cycloalkyl.

In certain embodiments (IIIb), R is benzyl; R$_1$ and R$_2$ are both methyl; R$_4$ is ethyl; and X is a meta-xylyl diradical (—CH$_2$(C$_6$H$_4$)CH$_2$—).

The invention includes methods of detecting an amine-containing analyte in a biological sample comprising contacting the biological sample with a compound of any of the formulas described above, and detecting the presence or absence of fluorescence in the sample, wherein the presence of fluorescence indicates the presence of an amine in the sample. The method can include measuring the amount of fluorescence in the sample and correlating the amount of fluorescence in the sample with a concentration of the amine in the sample.

By the term "independently", the skilled artisan will appreciate that each and every group may be selected from the entire list set forth as possible selections without regard to the selections of other groups having the same or different appellations.

As used herein the term "alkyl" refers to C$_1$-C$_{10}$ inclusive, linear, branched, or cyclic, saturated or unsaturated (i.e., alkenyl and alkynyl) hydrocarbon chains. The alkyl group can be optionally substituted with one or more (e.g., one to about five, or one to about three) alkyl group substituents which can be the same or different, where "alkyl group substituent" includes alkyl, halo, arylamino, acyl, hydroxyl, aryloxy, alkoxyl, alkylthio, arylthio, aralkyloxy, aralkylthio, carboxy, alkoxycarbonyl, oxo, or cycloalkyl. There can be optionally inserted along the alkyl chain one or more (e.g., one to about ten, one to about five, or one to about three) oxygen, sulfur or substituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to linear alkyl chain.

"Aryl" refers to an aromatic substituent that may be a single ring or multiple rings that are fused together, linked covalently, or linked to a common group such as an ethylene, methylene or oxy moiety. The aromatic rings of the aryl group may each and optionally contain heteroatoms, for example, as in pyridine, pyrazine, or imidazole. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, acyl, halo, nitro, alkoxycarbonyl, aryloxycarbonyl, arylalkoxycarbonyl, acyloxyl, acylamino, aroylamino, carbamoyl, alkylcarbamoyl, dialkylcarbamoyl, arylthio, alkylthio, alkylene, boronic acid, and —NRR', where R and R' can be each independently hydrogen, alkyl, aryl and aralkyl. Therefore, the term "aryl" includes alkaryl, aralkyl, and alkyl(aralkyl).

"Cyclic" and "cycloalkyl" refer to a non-aromatic mono- or multicyclic ring system of about 3 to about 10 carbon atoms. The cycloalkyl group can be optionally partially unsaturated. The cycloalkyl group can be also optionally substituted with any alkyl substituent as described above. There can be optionally inserted along the cyclic alkyl chain one or more oxygen, sulfur or substituted nitrogen atoms, wherein the nitrogen substituent is hydrogen, lower alkyl, or aryl, thus providing a heterocyclic group.

Figure 2:
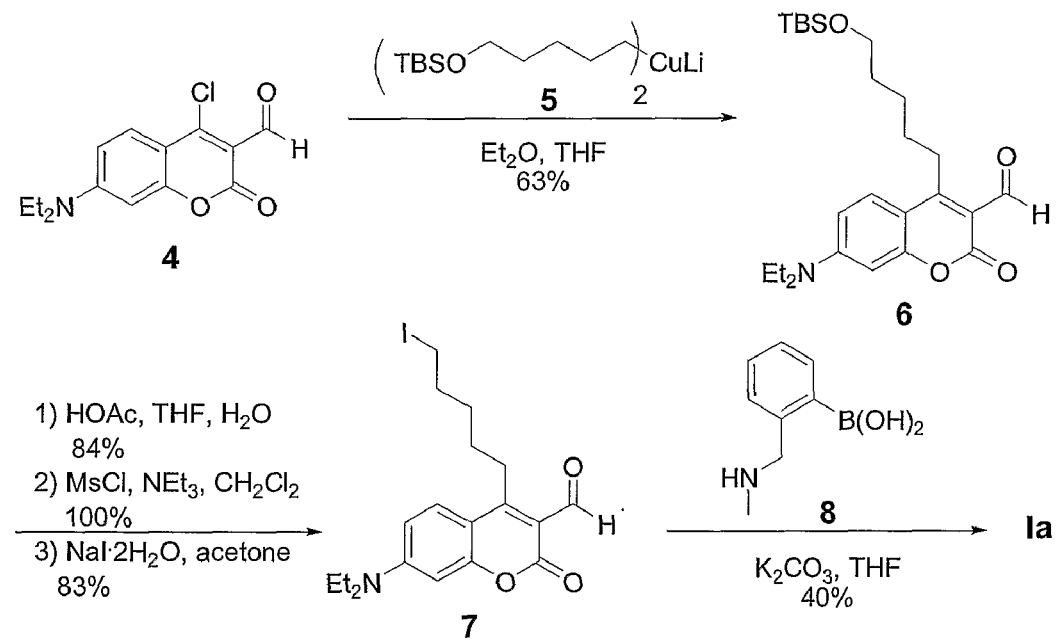
FIG. 2 depicts Scheme 1, which outlines a general synthesis of Coumarin-based sensors (I).

A representative synthesis of the inventive coumarin-based sensors is illustrated as Scheme I in FIG. 2. A TBS-protected alcohol 6 is produced from 4-chloro-7-diethylamino-3-formyl coumarin (4) and cuprate 5. The TBS-protected alcohol 6 is converted to iodide 7 in three steps via the mesylate. A final alkylation with aminomethyl phenylboronic acid (8) yields the Coumarin-based sensor. This general synthesis is further described in the Examples section below, particularly in the synthesis of Ia.

Figure 3:
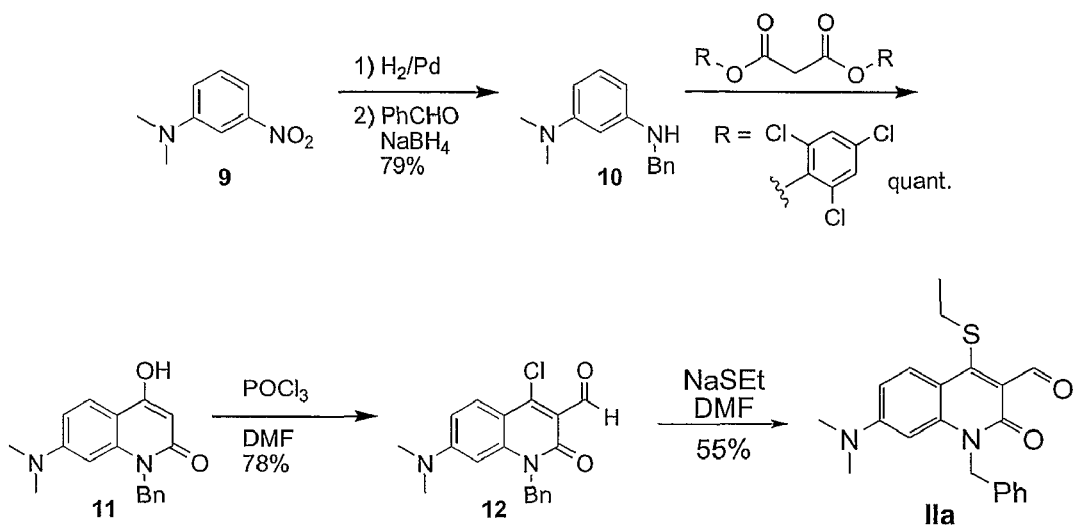
FIG. 3 depicts Scheme 2, which outlines a general synthesis of Quinolone-based sensors (II).

A representative synthesis of the inventive quinolone-monomer sensors is illustrated as Scheme 2 in FIG. 3. The quinolone core 11 is prepared in 4 steps from 3-nitro-dimethylaniline (9) following close analogy to the coumarin series (Scheme 1). The core 11 is then treated with thiolates in a Michael-Addition fashion to produce the quinolone-monomer sensors. The general synthesis is further described in the Examples section below, particularly in the synthesis of IIa and IIb.

Figure 4:
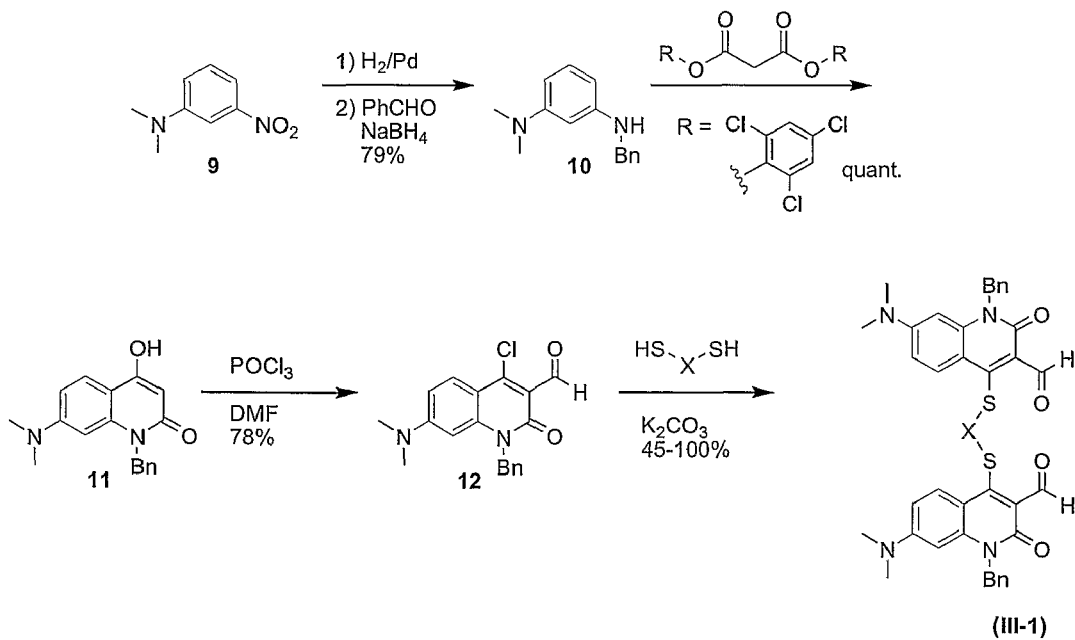
FIG. 4 depicts Scheme 3, which outlines a general synthesis of Quinolone-dimer-based sensors (III).

A representative synthesis of the inventive quinolone-dimer-based sensors is illustrated as Scheme 3 in FIG. 4. The quinolone core 11 is prepared in the same way as the monomer sensor, and then compound 11 can be treated with different thiolates in a Michael-Addition fashion to produce thio-ethers, the dimer sensors. To access diamine sensors, compound 12 has been treated with several dithiols to produce a series of quinolone dimers III a-g, shown in Table 1 below.

TABLE 1

Chemical Structures of Quinolone Dimer Sensors III a-g.

| Dimer | -X- |
|---|---|
| III a | *p-xylylene linker* |
| III b | *m-xylylene linker* |
| III c | *o-xylylene linker* |
| III d | *m-phenylene dimethylene linker* |
| III e | *o-phenylene linker* |
| III f | *butylene linker* |
| III g | *hexylene linker* |

While Table 1 illustrates certain specific X groups, one skilled in the art will readily recognize that other X groups can be used to link the dimers, such as optionally substituted alkyl chains of various lengths, optionally substituted aryl groups with varying linker substitution (i.e., ortho, meta, or para), and aryl linkers with various length alkyl groups that link the cores of the dimers.

Figure 5:
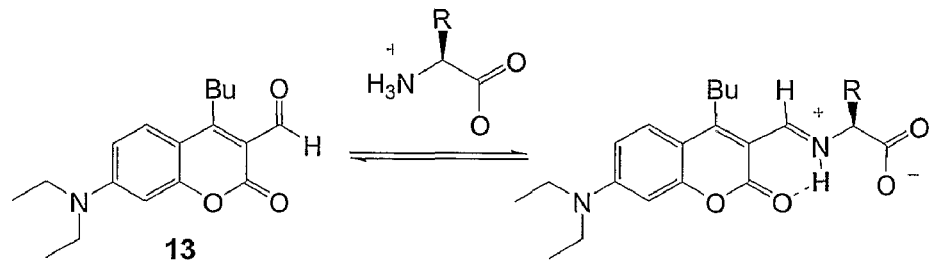
FIG. 5 depicts Scheme 4, which outlines the formation of an iminium ion between coumarin derivative 13 and a primary amine.

The inventive sensors are useful for selectively binding and thus detecting primary amine analytes. A previous investigation discovered that a certain coumarin aldehyde 13 could detect amines by reversible formation of an iminium ion, which activates a fluorescent response. More specifically, formation of an iminium ion between the aldehyde and an amine analyte produces a large chromophoric response due to an internal hydrogen bond with the coumarin carbonyl, as illustrated by Scheme 4 in FIG. 5. In addition, selective excitation of the iminium ion resulted in a substantial increase in fluorescent intensity upon titration with amines. Importantly, the previous study also showed that electron-poor aldehydes can serve as good recognition elements for amines under high-salt physiological conditions. However, the coumarin aldehyde 13 showed little discrimination among various primary amine guests, giving weak associations with most primary amines.

Figure 6A:
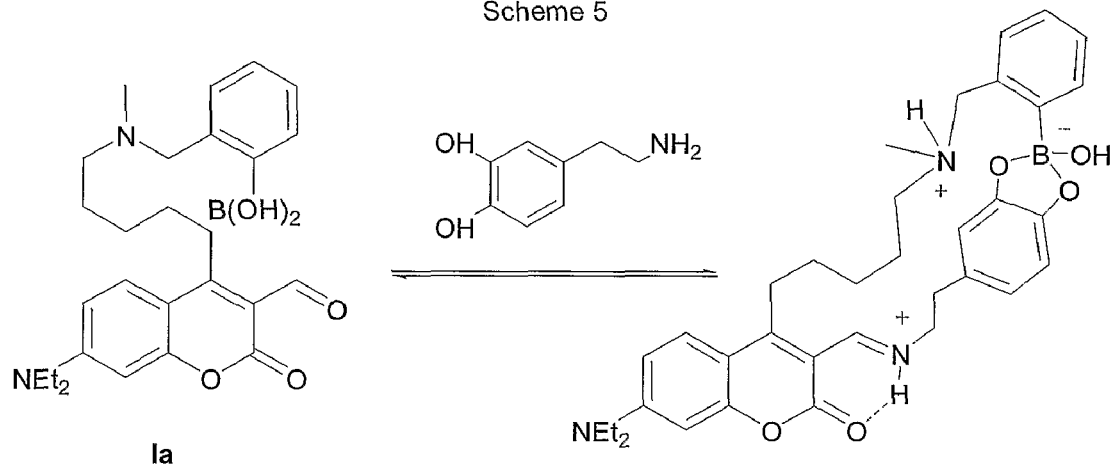
FIG. 6(a) depicts Scheme 5, which illustrates the binding between coumarin-based sensor (Ia) and dopamine.
Figure 6B:
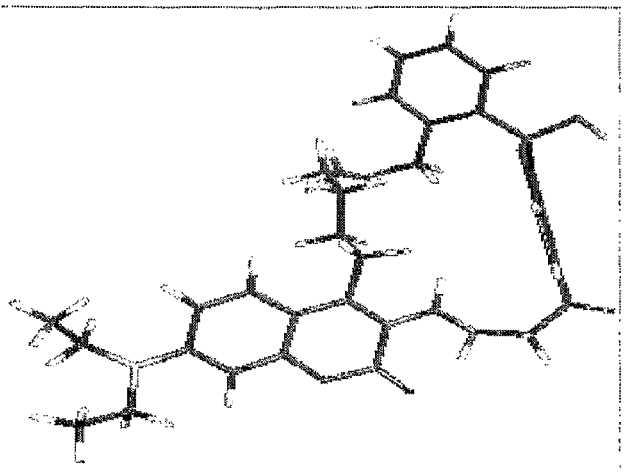
FIG. 6(b) shows a flexible spacer in the complex.

Described herein is a significantly modified coumarin aldehyde that resulted in coumarin-based sensors I that bind and detect catecholamines under physiological conditions. A boronic acid is incorporated as an additional recognition element to enhance both selectivity and affinity for dopamine over other primary amine competitors, as illustrated by Scheme 5 in FIG. 6(a). A flexible spacer between the coumarin and boronic acid is utilized to preserve the integrity of the internal hydrogen bond in the complex, as illustrated in FIG. 6(b).

The inventive coumarin-based sensors I are much improved over known catechol-containing-analyte sensors. The sensors I bind to primary catecholamines with good affinity and acts as an effective colorimetric sensor for dopamine and norepinephrine (the neurotransmitters) with excellent selectivity over epinephrine, amino acids, and glucose.

First, the sensors I produce a large chromophoric response when reacting with primary amines under physiological conditions. One exemplary coumarin-based sensor, 2-(((5-(7-(diethylamino)-3-formyl-2-oxo-2H-chromen-4-yl)pentyl)(methyl)amino)methyl)phenylboronic acid, sensor Ia, has been examined spectrophotometrically by titration with dopamine under neutral aqueous conditions in which a reducing agent is included to suppress oxidation of the air-sensitive catechol group.

Figure 7:
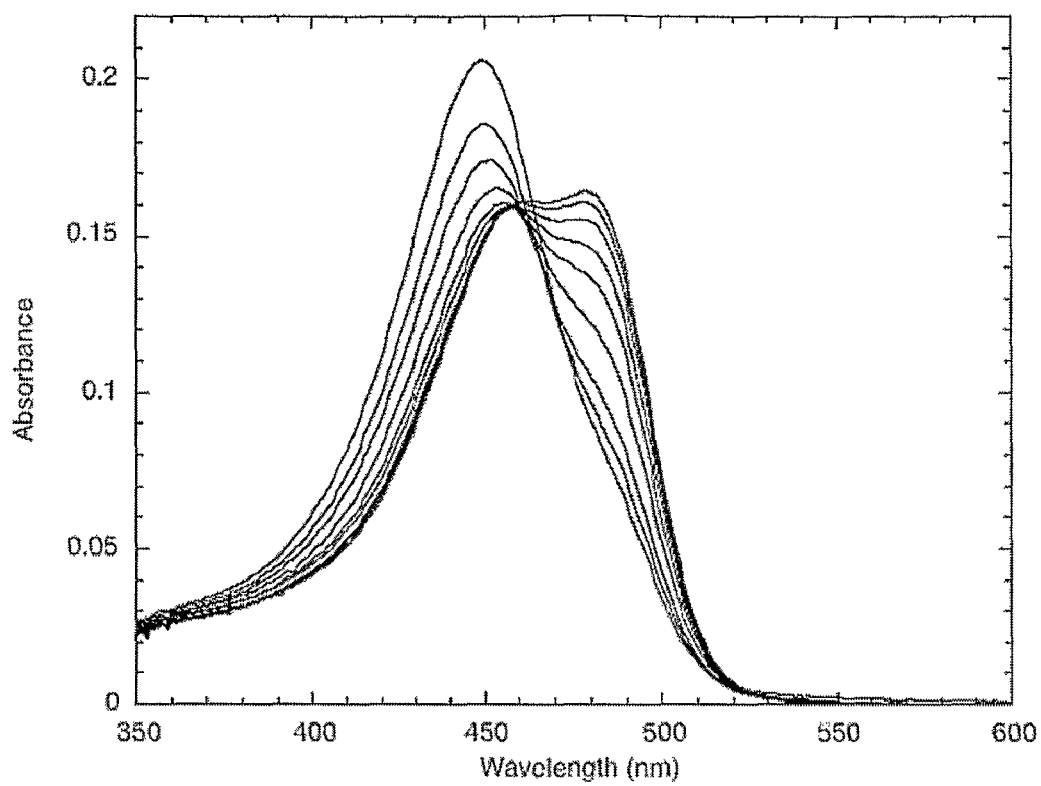
FIG. 7 shows UV-vis absorption titration of coumarin-based sensor (Ia) with dopamine.

The titration conditions are 10 μM sensor Ia with 100 mM $Na_2S_2O_3$, 50 mM HEPES, 20 mM NaCl, pH=7.0, and at 37° C. By UV-vis absorption, as illustrated in FIG. 7, sensor Ia gives a large red shift in absorption (445 nm to 480 nm). Sensor Ia is further titrated with other amine-containing analytes, and the changes in absorbance ($\Delta\lambda_{max}$) is listed in Table 2. All primary amines give similar shifts in absorbance, whereas glucose (lack of amino group) and epinephrine (secondary amine), give no shift in absorbance, since they do not interact with the aldehyde moiety. Therefore, the inventive coumarin-based sensors I are selective for primary amines. See also, *Org. Lett.* 2004, 6(21), 3727-3730, which is incorporated herein by reference.

TABLE 2

Association Constants and Spectroscopic Parameters for Titration of Sensor Ia with Various Analytes.

| guest | $\Delta\lambda_{m01}$ (nm) | $K_n$ $(M^{-1})^a$ | $I_{sat}/I_0^b$ ($\lambda_{ex}$ = 446 nm) | $I_{sat}/I_0^b$ ($\lambda_{ex}$ = 484 nm) | $I_{sat}/I_0^b$ ($\lambda_{ex}$ = 495 nm) |
|---|---|---|---|---|---|
| 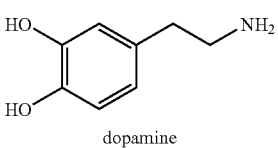 dopamine | 30 | 3400 | 0.50 | 0.60 | —$^c$ |
| 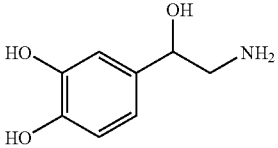 norepinephrine | 24 | 6500 | 0.39 | 0.46 | —$^c$ |
| 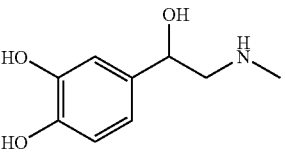 epinephrine | 0 | 5000 | 0.73 | 0.76 | 0.77 |
|  tyramine | 31 | 250 | 0.41 | 8.0 | 52 |
| 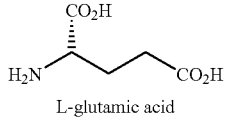 L-glutamic acid | 35 | 6.8 | 0.87 | 7.0 | 25 |
| 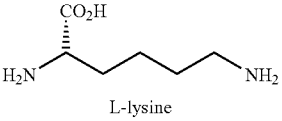 L-lysine | 36 | 4.0 | 0.75 | 8.0 | 25 |

TABLE 2-continued

Association Constants and Spectroscopic Parameters for Titration of Sensor Ia with Various Analytes.

| guest | $\Delta\lambda_{m01}$ (nm) | $K_n$ (M$^{-1}$)$^a$ | $I_{sat}/I_0^b$ ($\lambda_{ex}$ = 446 nm) | $I_{sat}/I_0^b$ ($\lambda_{ex}$ = 484 nm) | $I_{sat}/I_0^b$ ($\lambda_{ex}$ = 495 nm) |
|---|---|---|---|---|---|
| 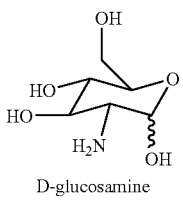 D-glucosamine | 39 | 5.0 | 0.55 | 5.9 | 27 |
| 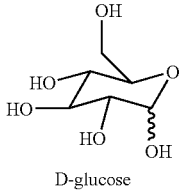 D-glucose | — | — | — | — | — |

$^a$$K_a$ measured by fluorescence spectroscopy, $\lambda_{ex}$ = 484 nm, $\lambda_{em}$ = 505 nm. Error in $K_a$ values are ± 20% based on triplicate titration.
$^b$$I_{sat}$ = fluorescence intensity at saturation taken from the theoretical fit to the binding isotherm.
$^c$Not determined.

Second, sensors I exhibit strong binding affinity with catecholamines over other amine-containing analytes. Binding constants ($K_a$) are determined by fluorescence titrations. In the exemplary case, exciting Ia at the 446 nm gives a change in fluorescence (some increase, some decrease) upon addition of all guests except glucose (which produced no chromophoric response). Fitting the decrease in fluorescence to a 1:1 binding isotherm gives the binding constants listed in Table 2.

As shown in Table 2, sensor Ia binds epinephrine and norepinephrine with similar efficiency even though the former does not form an iminium ion with the aldehyde, indicating that the boronic acid-catechol interaction is responsible for most of the affinity of the receptor. Tyramine, with only one phenolic hydroxyl group, has significantly reduced affinity; and other primary amines, such as glutamate lacking phenolic hydroxyl group, also exhibit low affinity. Even glucosamine, which possesses both an amine and a diol functionality, binds with affinity similar to the simple amines. Apparently, the geometry of sensor Ia is not suited to the compact aminosugar. Thus, the inventive coumarin-based sensors I exhibited both strong binding affinity and colorimetric response only to dopamine and norepinephrine. Epinephrine gave no color change, and other amines bound with 3 orders of magnitude lower affinity.

Figure 8:
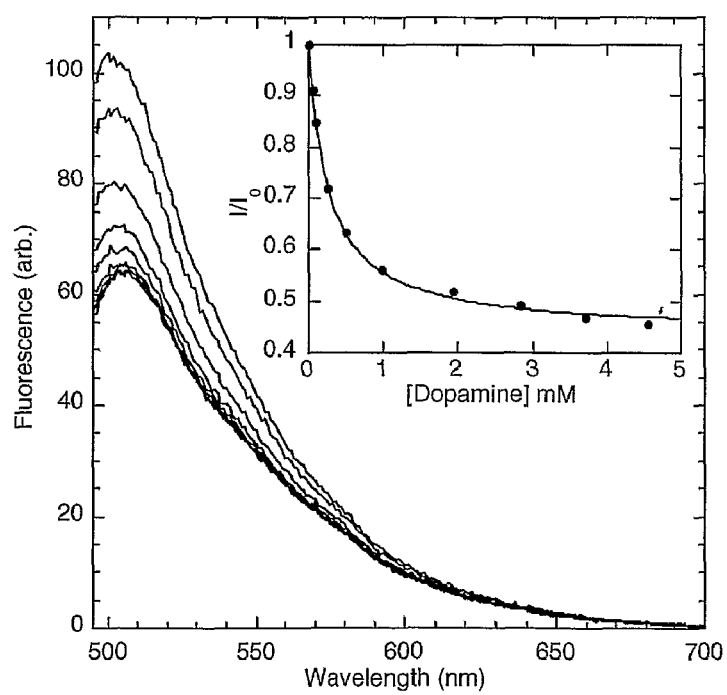
FIG. 8 shows fluorescence titration of Sensor Ia with dopamine at 484 nm.

Table 2 also lists the fluorescence response of the sensor Ia as $I_{sat}/I_0$ (the maximum fluorescence change at saturation) for three different excitation wavelengths: 446 nm, 484 nm, and 495 nm. By exciting sensor Ia at the aldehyde absorption maximum (446 nm), a decrease in fluorescence has been observed for all analytes because the sensor shifted from the aldehyde to the iminium ion form. At higher wavelengths of excitation, simple amines give the typical large increase in fluorescence since the iminium ion preferentially absorbs at these wavelengths. Interestingly, the fluorescence of sensor Ia is quenched upon binding dopamine, giving an overall decrease in emission when excited at 484 nm (FIG. 8). The fluorescence quenching effect is found to be directly related to the catechol group. The electron-rich catechol is likely acting as a photoinduced electron transfer (PET) quencher of the coumarin under these conditions, which makes coumarin-based sensors I potential "off" sensors but may limit their utilities as "on" sensors.

The present invention further provides Quinolone-Monomer Sensors II, which are more resistant to catechol-quenching effects discussed above. A simple monomer IIa, 1-benzyl-7-(dimethylamino)-4-(ethylthio)-2-oxo-1,2-dihydroquinoline-3-carbaldehyde, has been prepared and tested. Though sensor IIa is a non-selective sensor, when tested with amine-containing analytes, sensor IIa shows good fluorescence properties and is emissive even when binding to dopamine.

Figure 9:
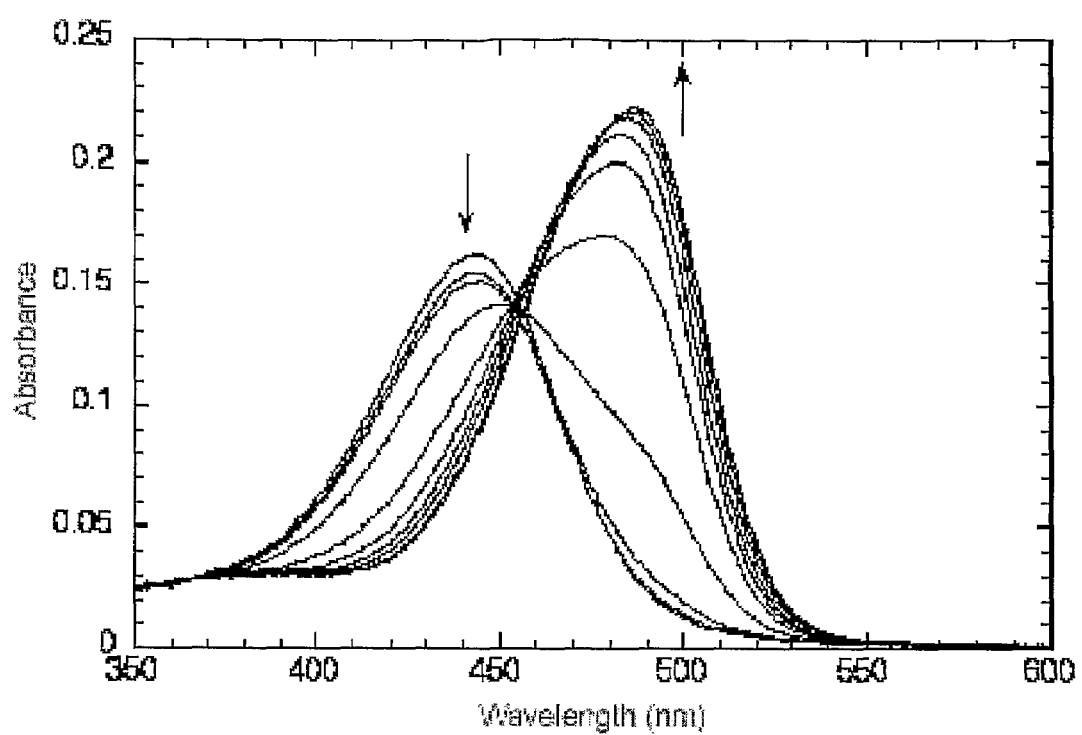
FIG. 9 shows UV-vis absorption titration of Sensor IIa with amines.

As shown in FIG. 9, Sensor IIa has the typical UV-vis response to binding amines and gives a seven fold increase in fluorescence when titrated with dopamine. The binding constant for dopamine (Ka=180 M−1) is similar to that for the binding to all primary amines, which makes the simple monomer IIa not a particularly great sensor in and of itself. However, testing of the monomer IIa proves that quinolone-based sensors can overcome the catechol-quenching effects.

The present invention further provides that the Quinolone-Monomer Sensors II can sense catecholamines and map their movements in a live cell. The initial proof of concept has been carried out by staining chromaffin cells with the simple monomer IIa. Specifically, several sets of chromaffin cells (which contain norepinephrine) were freshly prepared on coverslips and various concentrations of IIa in media were added. The optimal sensor concentration was found to be 0.5 μM with 15 minutes of equilibration time. Using confocal microscopy it can be seen that the cells are selectively stained by the sensor (FIG. 10).

Figure 10:
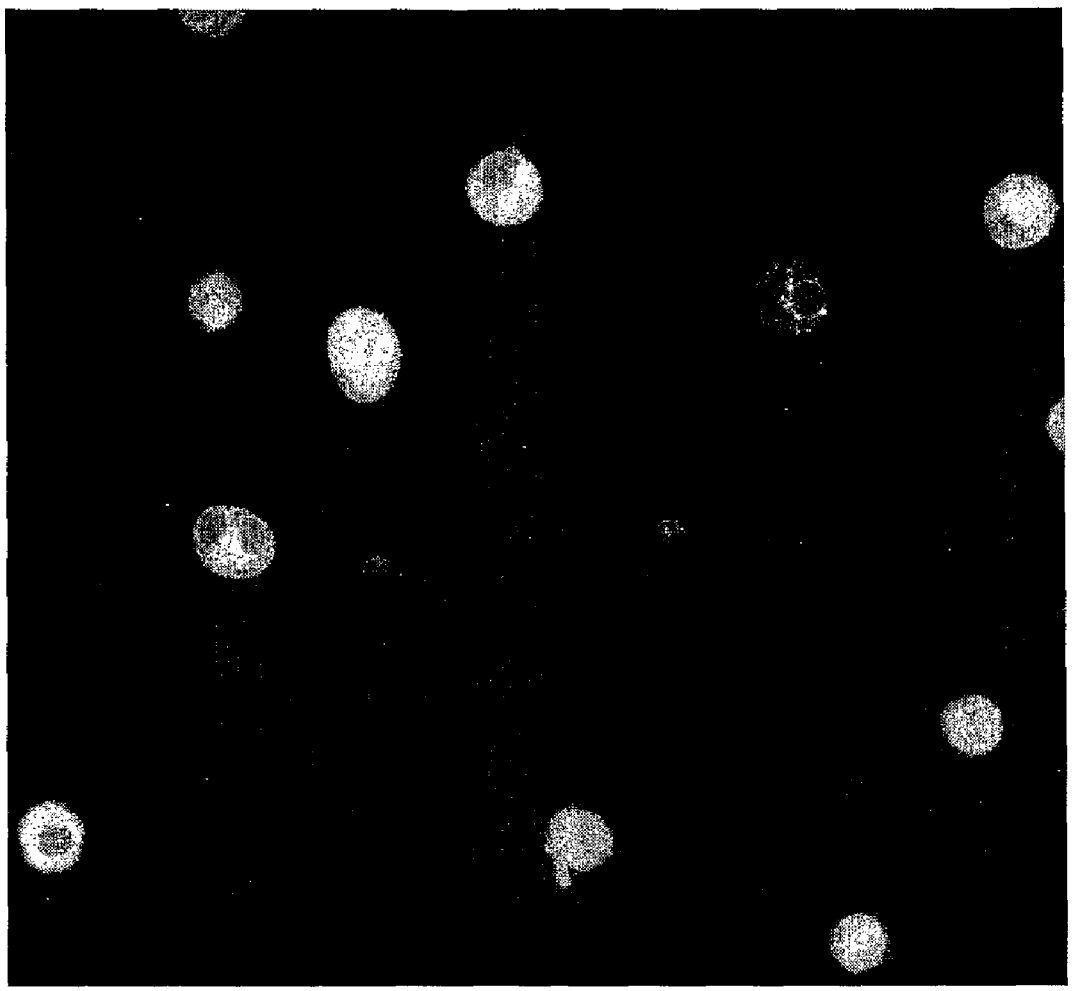
FIG. 10 shows chromaffin cell staining with Sensor IIa.

As illustrated in FIG. 10, the punctate staining (appearance of bright spots) is consistent with the presence of sensor IIa in the vesicles. The nuclei are clearly visible as dark regions. The sensor IIa can freely diffuse in cells, therefore the lack of staining in the nucleus is presumably because the nucleus lacks high concentrations of amines. These results are actually surprisingly good for a non-selective sensor.

Given that the sensor IIa binds equally well to all amines, it is likely that the sensor is actively accumulating in the vesicles. Sensor IIa is a neutral membrane permeable probe, but the catecholamine adduct is completely protonated in the acidic interior (pH=5.5) and cannot leave the vesicle. This selective membrane permeability combined with the unusually high concentration of catecholamine in the vesicle (1 M) causes the sensor to accumulate in the vesicle. Thus, the sensor is much more selective than its native affinity for amines would predict. There is obviously some cytosolic fluorescence from sensor bound to amines in the cytosol.

The present invention further discloses that Sensor IIb, 2-(((3-((1-benzyl-7-(dimethylamino)-3-formyl-2-oxo-1,2-dihydroquinolin-4-yl)methylthio)propyl)(methyl)amino) methyl)phenylboronic acid, exhibits selectivity between labeling primary and secondary amines in living cells. In particular, IIb labels norepinephrine-containing cells more brightly than it labels epinephrine-containing cells from the same adrenal glands.

The adrenal medulla contains two types of chromaffin cells; those that primarily contain norepinephrine within vesicles and those that primarily contain epinephrine. The two types of cells can be separated upon high-speed centrifugation in a Percoll density gradient. Following centrifugation, the less-dense norepinephrine enriched cells can be collected from the top of the gradient, whereas the denser epinephrine-enriched cells settle to the bottom. Norepinephrine-enriched cells stain more brightly than epinephrine enriched cells loaded with IIb under the same conditions (0.25 uM for 15 min.) and visualized under the same conditions using confocal microscopy.

It should be noted that acridine orange is commonly used to visualize synaptic vesicles because, as a weakly basic amine, it accumulates in acidic compartments via a similar mechanism. However, acridine orange accumulates in all acidic compartments (including endosomes, etc.). Sensor IIa is already a step ahead of that since IIa only stains acidic compartments which contain a high concentration of amines (neurotransmitters).

The present invention further discloses that the Quinolone-Dimer Sensors III can also provide detection for diamine analytes. The certain exemplary dimer sensors IIIa-g have been probed spectroscopically by UV-vis and fluorescence titration experiments. In general, the experimental data (listed in Table 3 below) shows good binding constants and excellent fluorescence enhancements. Moreover, by variation of the linker portion of the sensor III, useful selectivities for different length diamino-analytes have been achieved.

Figure 11A:
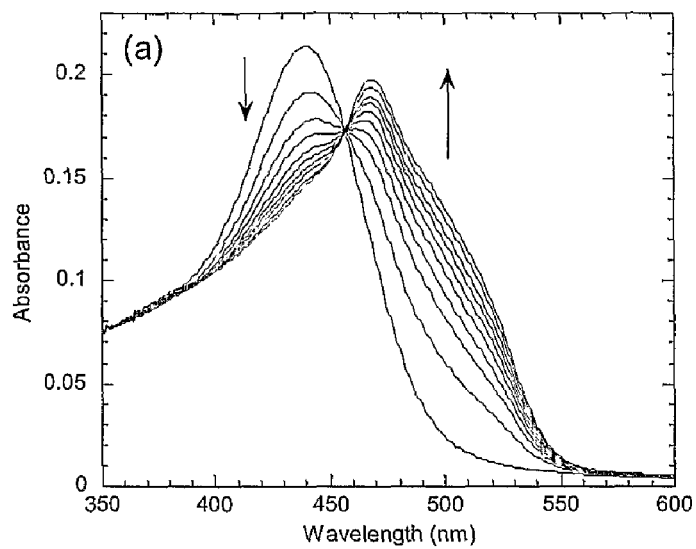
FIG. 11(a) shows UV-vis absorption titration of Sensor IIIg with diaminopropane.
Figure 11B:
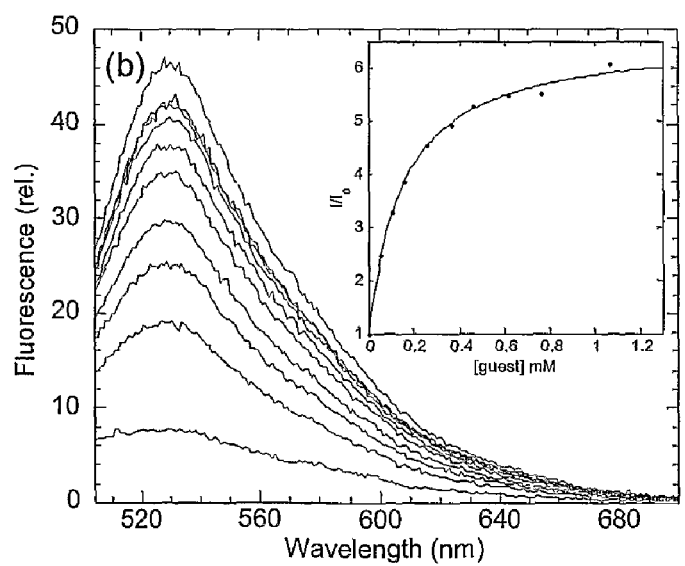
FIG. 11(b) shows fluorescence titration of Sensor IIIg with diaminopropane.

First, the absorption spectra show trends similar to those observed with the coumarin sensors in which a large red shift in absorption maximum is observed upon addition of diamines to the sensors. During the experiments, the dimer sensors have displayed poor water solubility properties compared to monomeric quinolones such as Ia; thus, spectroscopic analysis has been carried out in a 1:1 methanol-buffer system. As shown in FIG. 11(a), when sensor IIIg is titrated with diaminopropane, a 28 nm shift in absorbance is observed consistent with a shift from aldehyde to iminium ion forms. The red shift in absorption has been attributed to the hydrogen bond between the formed iminium ion and the carbonyl group of the chromophore. In fluorescence mode, by exciting the chromophore at 495 nm, a large increase in fluorescence was observed upon titration with the diamine (FIG. 11(b)). The fluorescence increase is fitted to a one-site binding isotherm which gave a binding constant of 6700 $M^{-1}$ with a maximum fluorescence increase at saturation ($I_{sat}/I_0$) of 6.6-fold. Results of titrations with six different guests for each of the eight sensors are tabulated in Table 3.

TABLE 3

Binding constants and maximum fluorescence enhancements for various amine guests binding to sensors IIIa-g and IIa.

| Sensor | Butylamine | | Diaminopropane | | Diaminobutane | | Diaminopentane | | Ornithine | | Lysine | |
| --- | --- | --- | --- | --- | --- | --- | --- | --- | --- | --- | --- | --- |
| | $K_a$ $(M^{-1})^a$ | $I_{sat}/I_0^b$ | $K_a$ $(M^{-1})$ | $I_{sat}/I_0$ | $K_a$ $(M^{-1})$ | $I_{sat}/I_0$ | $K_a$ $(M^{-1})$ | $I_{sat}/I_0$ | $K_a$ $(M^{-1})$ | $I_{sat}/I_0$ | $K_a$ $(M^{-1})$ | $I_{sat}/I_0$ |
| IIIa | 160 | 12 | 590 | 8.3 | 640 | 16 | 470 | 17 | 580 | 14 | 410 | 15 |
| IIIb | 93 | 20 | 820 | 14 | 600 | 21 | 620 | 19 | 1000 | 22 | 540 | 29 |
| IIIc | 130 | 13 | 3300 | 6.5 | 520 | 10 | 480 | 10 | 840 | 12 | 780 | 14 |
| IIId | 72 | 8.8 | 3400 | 16 | 1600 | 15 | 1200 | 15 | 3300 | 13 | 2100 | 4.7 |
| IIIe | 30 | 10 | 350 | 8.5 | 160 | 10 | 350 | 4.3 | 680 | 7.3 | 800 | 10 |
| IIIf | 31 | 26 | 2100 | 15 | 690 | 24 | 270 | 24 | 550 | 22 | 1460 | 24 |
| IIIg | 43 | 38 | 6700 | 6.6 | 1477 | 27 | 2200 | 18 | 2400 | 20 | 2756 | 27 |
| IIa | 76 | 32 | | | | | | | | | 129 | 41 |

$^a$Error in $K_a$ is ±20% based on duplicate titrations.
$^b I_{sat}/I_0$ is the maximum change in fluorescence derived from the theoretical fit to the binding isotherm.

Secondly, selectivity has been achieved. The data shown in Table 3 provide a number of trends in relative affinity. In all cases, the diamines bind better than butyl amine with the obvious exception of the monomer IIa. The extent of the difference varied from 2.5 fold for sensor IIIa to 160 fold for IIIg. The interesting feature of the series of sensors is their relative selectivity for the various guests/analytes. The range of binding constants for the different length guests varies over approximately an order of magnitude from 160-6700 $M^{-1}$. Between the xylene linked sensors IIIa-c, very little selectivity is observed except for the preference for the smaller ortho-linked sensor to bind the smaller diamine. The meta-linked sensor (IIb) demonstrated a small preference for ornithine which is coupled with a very large fluorescence increase (22 fold) for that guest.

Looking at the phenyl linked sensors IIId and IIIe, it is interesting to note that the meta-phenyl linked sensor has overall higher affinity for all guests compared to the ortho-phenyl linked sensor. In fact, IIId is selective between the amino acid guests with a preference for ornithine which is not observed for IIIe. Indeed, the maximum fluorescence change for IIId is much larger for ornithine than for lysine which may indicate a better binding geometry for ornithine which allows the hydrogen bonding necessary for large chromophoric changes. The most selective sensors of the group are the more flexible sensors IIIf and IIIg. Excluding diaminopropane, the preferred guest in both cases is lysine. Although the selectivity is higher for IIIf, the overall binding constant is higher for IIIg. Indeed, in both cases the fluorescence increase is much smaller for diaminopropane than the other guests. Thus, the sensors can distinguish guests based not only on the binding constant, but also on the relative fluorescence change which is induced.

The following Examples are intended to illustrate the invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Example 1

Synthesis of Coumarin Boronic Acid Sensor (Sensor Ia)

(1) Synthesis of TBSO-pentyl coumarin (compound 6 in Scheme 1). A solution of TBS-protected 5-iodopentanol (2.35 g, 7.15 mmol) and $Et_2O$ (70 mL) in a flame-dried, $N_2$-flushed flask was cooled to −78° C. tBuLi (10.0 mL, 1.5 M, 15.0 mmol) was added, and the mixture was stirred at −78° C. for 5 min. then ambient temperature for 1 h. The solution was cooled to 0° C., and CuI (681 mg, 3.58 mmol) was added. The mixture was stirred at 0° C. for 10 min; the mixture turned dark purple during this time. The reaction mixture was cooled to −78° C., and THF (35 mL) was added. Coumarin chloroaldehyde 4 (1.00 g, 3.58 mmol) in THF (35 mL) was added via cannula. The reaction was stirred under $N_2$ at −78° C. for 30 min. then quenched with saturated $NH_4Cl$ (75 mL). The mixture was extracted with $CH_2Cl_2$ (3×150 mL). The combined organic layers were dried over $MgSO_4$, and the solvent was removed in vacuo. The resulting yellow solid was purified via flash chromatography (EtOAc/hex, 10:90 to 15:85), and the product was isolated as a yellow solid (1.01 g, 63%).

Data for TBSO-pentyl coumarin: mp=103-105° C.; $^1H$ NMR (250 MHz, $CDCl_3$): δ 10.36 (s, 1H), 7.61 (d, J=9.3 Hz, 1H), dd (6.65, J=2.6, 9.3 Hz, 1H), 6.46 (d, J=2.6 Hz, 1H), 3.63 (t, J=5.9 Hz, 2H), 3.46 (q, J=7.1 Hz, 4H), 3.26 (t, J=7.9 Hz, 2H), 1.57-1.62 (m, 6H), 1.25 (t, J=7.1 Hz, 6H), 0.88 (s, 9H), 0.045 (s, 6H); $^{13}C$ NMR (62.5 MHz, $CDCl_3$): δ 190.2, 163.5, 162.7, 157.2, 152.4, 128.3, 111.1, 109.7, 108.1, 96.9, 62.6, 44.8, 32.2, 30.0, 27.4, 26.0, 25.7, 18.0, 12.2, −5.6; FTIR (neat): 2933, 2860, 1716, 1679, 1615, 1560, 1509, 1450, 1356, 1258, 1148.

HRMS: Calc. for $C_{25}H_{39}LiNO_4Si$ $(M+Li)^+$: 452.2808. Found: 452.2806.

(2) Synthesis of Coumarin pentyl alcohol. $H_2O$ (22 mL) and AcOH (66 mL) were added to a solution of TBSO-pentyl coumarin 6, (1.00 g, 2.24 mmol) in THF (22 mL). The mixture was stirred at ambient temperature for 2 h. The reaction mixture was quenched with solid $K_2CO_3$ to pH=8, extracted with $CH_2Cl_2$ (3×150 mL), dried on $MgSO_4$, and the solvent was removed in in vacuo. The resulting yellow-orange solid was purified via flash chromatography (EtOAc/hex, 20:80 to 80:20), and the product was isolated as a yellow solid (622 mg, 84%).

Data for Coumarin pentyl alcohol: mp=122-123° C.; $^1H$ NMR (250 MHz, $CDCl_3$): δ 10.3 (s, 1H), 7.62 (d, J=9.4 Hz, 1H), 6.66 (dd, J=2.5, 9.3 Hz, 1H), 6.44 (d, J=2.5 Hz, 1H), 3.68 (t, J=5.6 Hz, 2H), 3.47 (q, J=7.1 Hz, 4H), 3.25 (t, J=6.8 Hz, 2H), 2.10 (s, 1H), 1.62-1.69 (m, 6H), 1.25 (t, J=7.1 Hz, 6H); $^{13}C$ NMR (62.5 MHz, $CDCl_3$): δ 190.7, 163.8, 163.1, 157.4, 152.6, 128.5, 111.3, 109.9, 108.3, 97.1, 62.5, 45.0, 32.2, 30.1, 27.6, 26.2, 12.4; FTIR (neat): 2932, 1709, 1675, 1612, 1556, 1505, 1447, 1354, 1268, 1203, 1147.

HRMS: Calc. for $C_{19}H_{25}LiNO_4$ $(M+Li)^+$: 338.1944. Found: 338.1946.

(3) Synthesis of Coumarin pentyl mesylate. A solution of the alcohol (622 mg, 1.88 mmol), $CH_2Cl_2$ (30 mL), and $NEt_3$ (800 μL, 5.69 mmol) in a flame-dried, $N_2$-filled flask was cooled to 0° C. MsCl (300 μL, 3.88 mmol) was added. The reaction was stirred under $N_2$ at 0° C. for 20 min. The solvent was removed in vacuo. The resulting yellow solid was purified via flash chromatography (EtOAc:hex, 40:60 to 50:50), and the product was isolated as a yellow solid (768 mg, 100%).

Data for Coumarin pentyl mesylate: mp=96-97° C.; $^1H$ NMR (250 MHz, $CDCl_3$): δ 10.30 (s, 1H), 7.61 (d, J=9.3 Hz, 1H), 6.69 (dd, J=2.5, 9.3 Hz, 1H), 6.43 (d, J=2.5 Hz, 1H), 4.29 (t, J=6.4 Hz, 2H), 3.48 (q, J=7.1 Hz, 4H), 3.23 (t, J=7.2 Hz, 2H), 3.06 (s, 3H), 1.87 (p, J=6.4 Hz, 2H), 1.63-1.66 (m, 4H), 1.26 (t, J=7.1 Hz, 6H); $^{13}C$ NMR (62.5 MHz, $CDCl_3$): δ 190.3, 163.0, 162.7, 157.2, 152.5, 128.2, 111.0, 109.9, 108.0, 96.9, 69.8, 44.8, 36.9, 29.3, 28.3, 27.1, 25.4, 12.2; FTIR (neat): 2935, 1708, 1674, 1613, 1557, 1506, 1449, 1351, 1267, 1203, 1171, 1115.

HRMS: Calc. for $C_{20}H_{27}LiNO_6S$ $(M+Li^+)$: 416.1719. Found: 416.1700.

(4) Synthesis of Coumarin pentyl iodide (compound 7 in Scheme 1). NaI (697 mg, 3.75 mmol) was added to a solution of the mesylate (768 mg, 1.88 mmol) in acetone (25 mL). The mixture was stirred at ambient temperature for 13 h. The solvent was removed in vacuo, and the resulting yellow solid was dissolved in $CH_2Cl_2$ (100 mL) and $H_2O$ (100 mL). The layers were separated, and the aqueous phase was extracted with $CH_2Cl_2$ (2×100 mL). The combined organic extracts were dried on $MgSO_4$, and the solvent was removed in vacuo. The resulting yellow solid was purified via flash chromatography (EtOAc:hex, 20:80 to 25:75), and the product was isolated as a yellow solid (648 mg, 83%).

Data for Coumarin pentyl iodide: mp=104-106° C.; $^1H$ NMR (250 MHz, $CDCl_3$): δ 10.35 (s, 1H), 7.60 (d, J=9.3 Hz, 1H), 6.66 (dd, J=2.4, 9.3 Hz, 1H), 6.46 (d, J=2.3 Hz, 1H), 3.47 (q, J=7.1 Hz, 4H), 3.20-3.26 (m, 4H), 1.92 (p, J=6.7 Hz, 2H), 1.62-1.63 (m, 4H), 1.25 (t, J=7.1 Hz, 6H; $^{13}C$ NMR (62.5 MHz, $CDCl_3$): δ 190.8, 163.4, 163.4, 157.6, 152.6, 128.4, 111.6, 109.9, 108.4, 97.3, 45.1, 32.9, 30.8, 29.2, 27.5, 12.5, 6.8; FTIR (neat): 1711, 1674, 1213, 1557, 1506, 1446, 1383.

HRMS: Calc. for $C_{19}H_{24}ILiNO_3$ $(M+Li^+)$: 448.0961. Found: 448.0961.

(5) Synthesis of Coumarin boronic acid sensor (Sensor Ia). Compound 7 (85 mg, 0.194 mmol), amine 8 (47 mg, 0.285 mmol), and $K_2CO_3$ (134 mg, 0.968 mmol) were placed in a sealed vessel with THF (2 mL). The mixture was stirred at 48° C. for 14 h. The mixture was cooled, poured onto $H_2O$ (10 mL), extracted with $CH_2Cl_2$ (3×10 mL), dried on $MgSO_4$, and the solvent was removed in vacuo. The resulting yellow solid was purified by HPLC (Xorbax XDB-C18 column, 0.1% TFA/$H_2O$: 0.1% TFA/MeCN, 90:10 to 0:100) The product was isolated as a yellow solid (37.4 mg, 40%).

Data for Coumarin boronic acid sensor: mp=92-94° C.; $^1H$ NMR (250 MHz, MeOH-d4): δ 10.21 (s, 1H), d (7.76, J=9.4 Hz, 1H), 7.57 (d, J=6.8 Hz, 1H), 7.10-7.26 (m, 3H), 6.28 (dd, J=2.6, 9.4 Hz, 1H), 6.52 (d, J=2.6 Hz, 1H), 4.09 (s, 2H), 3.53 (q, J=7.1 Hz, 4H), 2.98 (t, J=8.2 Hz, 2H), 2.57 (s, 3H), 1.78-1.85 (m, 2H), 1.59 (m, 4H), 1.23 (t, J=7.1 Hz, 6H); $^{13}C$ NMR (125 MHz, MeOH-d4): δ 191.7, 165.6, 165.1, 159.1, 154.8, 134.8, 133.6, 132.4, 130.2, 129.9, 128.5, 127.6, 112.0, 111.8, 109.5, 98.0, 64.1, 56.4, 46.0, 40.2, 31.1, 28.3, 28.2, 24.6, 12.8; FTIR (neat): 1704, 1673, 1610, 1555, 1503, 1444, 1351, 1263, 1201, 1140.

HRMS: Calc. for $C_{27}H_{36}BN_2O_5$ $(M+H)^+$: 479.2712. Found: 529.2834.

Example 2

Synthesis of Thioethyl Quinolone (Sensor IIa)

(1) Synthesis of 4-Hydroxy Quinolone (compound 11 in Schemes 2 and 3). $N^1,N^1$-dimethyl-$N^3$-benzylaniline (4.39 g, 19.4 mmol), bis(2,4,6-trichlorophenyl)malonate (8.98 g, 19.4 mmol), and toluene (150 mL) were added to a flame-dried flask. A reflux condenser and drying tube were attached, and the mixture was refluxed for 20 h. The reaction mixture was cooled and filtered. The filtrate was washed with hexanes to yield the title compound as tan a powder (5.8 g, 100%).

Data for 4-Hydroxy Quinolone: mp=284°-286°, decomp.; $^1$H NMR (250 MHz, DMSO-d6): δ11.0 (1H, s), 7.65 (1H, d, J 9.0), 7.19-7.28 (5H, m), 6.59 (1H, dd, J 2.0 and 9.0), 6.29 (1H, d, J 1.9), 5.69 (1H, s), 5.40 (2H, s) and 2.86 (6H, s); $^{13}$C NMR (62.5 MHz, DMSO-d6): δ 163.5, 161.9, 152.0, 140.8, 137.9, 128.4, 126.8, 126.7, 124.1, 107.1, 105.9, 96.2, 93.4, 43.9, 39.6; FTIR (neat): 1625, 1569, 1544, 1537, 1488, 1384, 1354.

HRMS Calc. for $C_{18}H_{18}LiN_2O_2$(M+Li)$^+$: 301.1528. Found: 301.1529.

(2) Synthesis of Quinolone Chloroaldehyde (compound 12 in Schemes 2 and 3): $POCl_3$ (6.2 mL, 66.5 mmol) was added to DMF (13 mL, 168 mmol) at 0° in a dry flask equipped with a drying tube. The solution was stirred at 0° for 15 minutes then at ambient temperature for 3.5 h. DMF (250 mL) then 4-hydroxy quinolone (13.8 g, 46.9 mmol) were added. The mixture was stirred at ambient temperature for 42 h. The resulting yellow suspension was poured onto $H_2O$ (800 mL) and filtered. The filtrate was washed with MeOH (800 mL). The resulting yellow solid was 90% pure and was used in subsequent reactions. A portion of the material was purified via flash chromatography ($Et_2O/CH_2Cl_2$, 0:100 to 10:90) for characterization.

Data for Quinolone Chloroaldehyde: mp=224.5°-226°; $^1$H NMR (300 MHz, CDCl$_3$): δ 10.55 (1H, s), 8.00 (1H, d, J 9.4), 7.24-7.34 (5H, m), 6.64 (1 H, dd, J 2.3 and 9.4), 6.20 (1H, d, J 2.3), 5.49 (2H, s), 3.00 (6H, s); $^{13}$C NMR (75 MHz, CDCl$_3$): δ 189.5, 162.3, 153.8, 148.4, 142.3, 136.0, 134.2, 129.8, 128.9, 127.5, 126.8, 116.0, 109.6, 95.3, 46.2, 40.1; FTIR (neat): 1682, 1637, 1611, 1583, 1558, 1514, 1496, 1454.

HRMS Calc. for $C_{19}H_{17}ClLiN_2O_2$ (M+Li)$^+$: 347.1139. Found 347.1144.

(3) Synthesis of Thioethyl Quinolone (Sensor IIa). Quinolone chloroaldehyde (200 mg, 0.715 mmol) and $K_2CO_3$ (494 mg, 3.58 mmol) in a $N_2$-flushed flask were dissolved in 5% $H_2O$/DMF (7.2 mL, degassed by 3× freeze-pump-thaw cycles). Ethyl disulfide (53 μL, 0.429 mmol) then PBu$_3$ (430 μL, 1.72 mmol) were added. The reaction was stirred at ambient temperature under $N_2$ 19 h. then $CH_2Cl_2$ (7 mL) and $H_2O$ (7 mL) were added. The mixture was extracted with $CH_2Cl_2$ (3×20 mL), and the combined organic extracts were washed with brine (20 mL) then dried on MgSO$_4$. The solvent was removed in vacuo, and the resulting yellow solid was purified via flash chromatography ($Et_2O/CH_2Cl_2$, 0:100 to 5:95). The product was isolated as a yellow solid (72.6 mg, 55%).

Data for Thioethyl Quinolone (Sensor IIa): mp=163-164° C.; $^1$H NMR (300 MHz, CDCl$_3$): δ 10.6 (s, 1H), 8.30 (d, J=9.3 Hz, 1H), 7.22-7.29 (m, 5H), 6.62 (dd, J=2.1, 9.3 Hz, 1H), 6.20 (d, J=2.1 Hz, 1H), 5.50 (s, 2H), 3.20 (t, J=6.7 Hz, 2H), 3.11 (t, J=6.9, 2H), 2.98 (s, 6H), 2.03 (1, J=6.8 Hz, 2H); $^{13}$C NMR (75 MHz, CDCl$_3$): δ 190.2, 162.2, 153.7, 153.5, 141.9, 136.1, 130.7, 128.7, 127.2, 126.7, 120.2, 112.3, 109.1, 95.6, 46.1, 40.0, 38.3, 33.2, 4.2; FTIR (neat): 1687, 1681, 1597, 1498, 1483, 1457, 1430, 1391.

HRMS: Calcd for $C_{21}H_{22}N_2O_2SLi$ (M+Li)$^+$:373.1562. Found: 373.1575.

Example 3

Synthesis of S-Linked Quinolone Boronic Acid Sensor IIb

Figure 12:
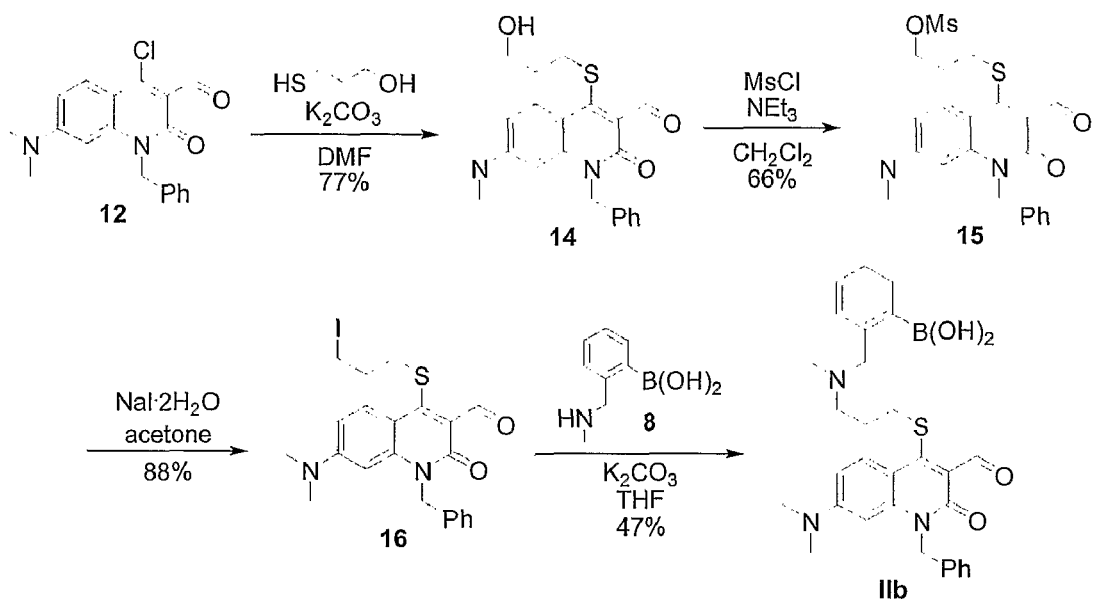
FIG. 12 shows additional synthetic steps to prepare Sensor IIb.

Sensor IIb is synthesis according to the Scheme 6 in FIG. 12.

(1) Synthesis of S-linked Quinolone Alcohol (compound 14 in Scheme 6). Quinolone chloroaldehyde (1.00 g, 2.94 mmol), $K_2CO_3$ (2.0 g, 14.7 mmol), and DMF (30 mL) were combined in a flame-dried, $N_2$-filled flask. 3-mercaptopropanol (380 μL, 4.40 mmol) was added, and the mixture was stirred at ambient temperature under $N_2$ for 17 hours. The reaction mixture was then poured onto $H_2O$ (150 mL) and extracted with $CH_2Cl_2$ (3×100 mL). The combined organic extracts were washed with brine (100 mL) then dried on MgSO$_4$. The solvent was removed in vacuo, and the resulting yellow solid was purified via flash chromatography (EtOAc then EtOAc/$CH_2Cl_2$, 50:50). The product was isolated as a yellow solid (892.5 mg, 77%).

Data for S-linked Quinolone Alcohol: mp=182.5-183° C.; $^1$H NMR (500 MHz, CDCl$_3$): δ 10.60 (s, 1H), 8.40 (d, J=9.3 Hz, 1H), 7.24-7.33 (m, 5H), 6.64 (dd, J=2.4 Hz, 9.3 Hz, 1H), 6.24 (d, J=2.4 Hz, 1H), 5.52 (s, 2H), 3.76 (q, J=5.8 Hz, 2H), 3.14 (t, J=7.0 Hz, 2H), 2.99 (s, 6H), 1.83-1.90 (m, 2H); $^{13}$C NMR (125 MHz, CDCl$_3$): δ 190.6, 162.6, 154.7, 153.7, 142.1, 136.4, 131.0, 128.8, 127.4, 126.8, 120.5, 112.7, 109.1, 95.8, 61.0, 46.3, 40.1, 34.8, 32.4; FTIR (neat) 3421, 2925, 1685, 1597, 1497, 1392, 1170.

HRMS calc. for $C_{22}H_{24}N_2O_3Li$ (M+Li)$^+$: 403.1668, found 403.1669.

(2) Synthesis of S-linked Quinolone Mesylate (compound 15 in Scheme 6). S-linked quinolone alcohol (430 mg, 1.08 mmol) in a flame-dried, $N_2$-filled flask was dissolved in $CH_2Cl_2$ (30 mL). The solution was cooled to 0°, then NEt$_3$ (460 μL, 3.27 mmol) and MsCl (160 μL, 2.07 mmol) were added. The reaction was stirred at 0° C. under $N_2$ for 20 min., then the solvent was removed in vacuo.

The resulting yellow solid was purified via flash chromatography (EtOAc/hex, 30:70 to 80:20), and the product was isolated as a yellow solid (337.8 mg, 66%). An analytically pure sample was isolated by recrystallization from PhMe.

Data for S-linked Quinolone Mesylate: $^1$H NMR (500 MHz, CDCl$_3$): δ 10.59 (s, 1H), 8.35 (d, J=9.3 Hz, 1H), 7.24-7.31 (m, 5H), 6.65 (dd, J=2.4 Hz, 9.4 Hz, 1H), 6.24 (d, J=2.3 Hz, 1H), 5.51 (s, 2H), 4.29 (t, J=6.1 Hz, 2H), 3.15 (t, J=7.0 Hz, 2H), 3.00 (s, 6H), 2.98 (s, 3H), 2.00-2.05 (m, 2H); $^{13}$C NMR (125 MHz, CDCl$_3$): δ 190.4, 162.6, 153.7, 153.3, 142.2, 136.2, 130.9, 128.8, 127.4, 126.8, 120.4, 112.5, 109.3, 95.8, 67.8, 46.3, 40.1, 37.4, 33.8, 29.4; FTIR (neat): 2931, 1597, 1498, 1391, 1353, 1171.

HRMS calc. for $C_{23}H_{26}N_2O_5S_2Li$ (M+Li)$^+$: 481.1443, found 481.1460.

(3) Synthesis of S-linked Quinolone Iodide (compound 16 in Scheme 6). Mesylate (605 mg, 1.28 mmol) and NaI.2H$_2$O (1.3 g, 6.99 mmol) were added to a flask and dissolved in acetone (17 mL). The mixture was stirred at ambient temperature for 16 hours, then the solvent was removed in vacuo. The residue was brought up in $CH_2Cl_2$ (30 mL) and $H_2O$ (30 mL). The layers were separated, and the aqueous layer was extracted with $CH_2Cl_2$ (2×30 mL). The combined organic extracts were dried on MgSO$_4$, and the solvent was removed in vacuo. The resulting yellow solid was purified via flash chromatography (EtOAc/hex, 20:80 to 40:60). The product was isolated as a yellow solid (554.9 mg, 88%).

Data for S-linked Quinolone Iodide: mp=143.5-145° C.; $^1$H NMR (300 MHz, CDCl$_3$): δ 10.60 (s, 1H), 8.30 (d, J=9.3 Hz, 1H), 7.22-7.29 (m, 5H), 6.62 (dd, J=2.1 Hz, 9.3 Hz, 1H), 6.20 (d, J=1.9 Hz, 1H), 5.50 (s, 2H), 3.20 (t, J=6.7 Hz, 2H), 3.11 (t, J=6.9 Hz, 2H), 2.98 (s, 6H), 2.03 (q, J=6.8 Hz, 2H); $^{13}$C NMR (75 MHz, CDCl$_3$) δ 190.2, 162.2, 153.7, 153.5, 141.9, 136.1, 130.7, 128.7, 127.2, 126.7, 120.2, 112.3, 109.1, 95.6, 46.1, 40.0, 38.3, 33.2; FTIR (neat): 1674, 1596, 1498, 1483, 1390.

HRMS calc. for $C_{22}H_{23}IN_2O_2SLi$ (M+Li)$^+$: 513.0685, found 513.0662.

(4) Synthesis of S-linked Quinolone Boronic Acid Sensor IIb. Iodide (221 mg, 0.448 mmol), amine (148 mg, 0.897 mmol), and K$_2$CO$_3$ (310 mg, 2.24 mmol) were added to a dry sealed tube. THF (4.5 mL) was added, and the tube was sealed and stirred at 40° C. for 17 hours. The mixture was cooled and poured onto H$_2$O then extracted with CH$_2$Cl$_2$ (3×30 mL). The combined organic extracts were dried on MgSO$_4$. The crude product was isolated as a yellow solid (268 mg), and a portion (33.7 mg) of the crude material was purified by HPLC (Xorbax XDB-C18 column, H$_2$O:MeCN, 75:25 to 0:100). The solvent was removed in vacuo, and the product was isolated as a yellow solid (25.1 mg, 47%).

Data for S-linked Quinolone Boronic Acid Sensor IIb: mp=131-134° C.; $^1$H NMR (500 MHz, MeOH-d4): δ 10.47 (s, 1H), 8.18 (d, J=9.3 Hz, 1H), 8.11 (d, J=9.3 Hz, 1H), 7.56 (d, J=10.1 Hz, 1H), 7.55 (d, J=7.8 Hz, 1H), 7.21-7.31 (m, 12H), 7.11-7.14 (m, 2H), 7.03-7.07 (m, 2H), 6.68-6.75 (m, 2H), 6.20-6.33 (m, 3H), 5.53 (br s, 4H), 3.98 (br s, 4H), 3.07 (t, J=6.7 Hz, 2H), 2.92-3.00 (m, 20H), 2.49 (br s, 2H), 1.95 (br s, 4H); $^{13}$C NMR (125 MHz, MeOH-d4): δ 191.3, 163.6, 163.3, 156.2, 155.5, 153.6, 153.4, 146.2, 143.1, 141.2, 140.9, 138.0, 137.7, 137.7, 134.7, 131.7, 131.7, 130.7, 130.7, 129.9, 129.9, 129.8, 128.6, 128.5, 128.5, 128.4, 128.0, 127.9, 127.9, 127.7, 127.2, 120.6, 116.6, 113.5, 113.1, 111.1, 110.8, 110.2, 99.5, 97.7, 97.4, 96.9, 63.8, 63.7, 60.5, 55.7, 40.3, 40.2, 40.0, 36.5, 34.7, 30.8, 25.8, 25.5; FTIR (neat): 2925, 2856, 1675, 1597, 1497, 1390, 1361.

HRMS calc. for $C_{30}H_{34}BN_3O_4SNa$ (M+Na)$^+$: 566.2261, found 566.2282.

Example 4

Synthesis of Sensor IIId, meta-Benzenedithiol Dimer

Chloroaldehyde (compound 12) (150 mg, 0.440 mmol), 1,3-benzenedithiol (28.5 mg, 0.200 mmol), K$_2$CO$_3$ (111 mg, 0.800 mmol), and DMF (12 mL) were combined in a flame-dried, N$_2$-filled flask. The reaction mixture was stirred at ambient temperature for 14 h then poured onto H$_2$O (20 mL) and extracted with CH$_2$Cl$_2$ (5×30 mL). The combined organic extracts were dried on MgSO$_4$, and the solvent was removed in vacuo. The resulting yellow solid was purified via flash chromatography (EtOAc/CH$_2$Cl$_2$, 0:100 to 30:70), and the product was isolated as a yellow solid (87.6 mg, 58%).

Data for Meta-Benzenedithiol Dimer (Sensor IIId): mp=224-226° C.; $^1$H NMR (500 MHz, CDCl$_3$): δ 10.48 (s, 2H), 7.96 (d, J=9.4 Hz, 2H), 7.25-7.32 (m, 10H), 6.99-7.12 (m, 4H), 6.52 (dd, J=2.4 Hz, 9.4 Hz, 2H), 6.23 (d, J=2.4 Hz, 2H), 5.55 (s, 4H), 2.97 (s, 6H); $^{13}$C NMR (125 MHz, CDCl$_3$): δ 190.1, 161.7, 153.5, 150.6, 142.5, 138.0, 136.3, 131.5, 129.9, 128.8, 127.4, 127.2, 126.8, 121.2, 110.9, 109.4, 95.7, 46.4, 40.0; FTIR (neat): 2927, 1694, 1598, 1503, 1390, 1364, 1164, 1169.

HRMS calc. for $C_{44}H_{38}N_4O_4S_2Li$ (M+Li)$^+$: 757.2495, found 757.2516.

Example 5

Staining Chromaffin Cells with the Simple Monomer IIa

FIG. 10 Shows sample staining of a mixed population of bovine adrenal chromaffin cells by the sensor IIa dye. A stock solution of 50 mM in DMSO was diluted in cell culture media to yield a final concentration of 0.5 uM. Cells were incubated in this solution at 37 C for 15 minutes and then the cells were washed with cell culture media without dye and observed using a confocal microscope at room temperature. The excitation wavelength was 488 nm.

Example 6

Staining Norepinephrine-Enriched Chromaffin Cells with Sensor IIb

Sensor IIb dye preferentially stains norepinephrine-enriched chromaffin cells. Following centrifugation of adrenal medullary cells in a Percoll density gradient, the less-dense norepinephrine enriched cells were collected from the top of the gradient, whereas the denser epinephrine-enriched cells were collected from the bottom of the gradient. Both collections of cells were incubated for 15 minutes at 37 C in 0.25 μM IIb dissolved in cell culture media. The cells were then washed in dye-free media and observed using a confocal microscope at room temperature.

Example 7

Sensor Selectivity Study

Successful results with a lysine sensor have been obtained. Quinolone chloroaldehyde 110 (Scheme 7) was chosen as a fluorescent core for an initial study. Addition of three different dithiols provided three dimer sensors (111a-c) without incident (45-73% yield unoptimized).

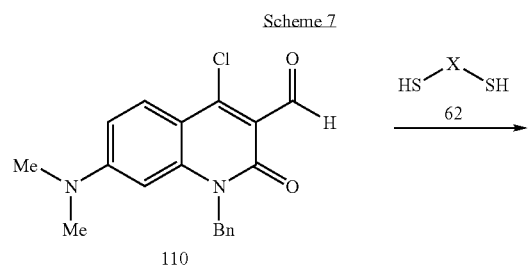

Scheme 7

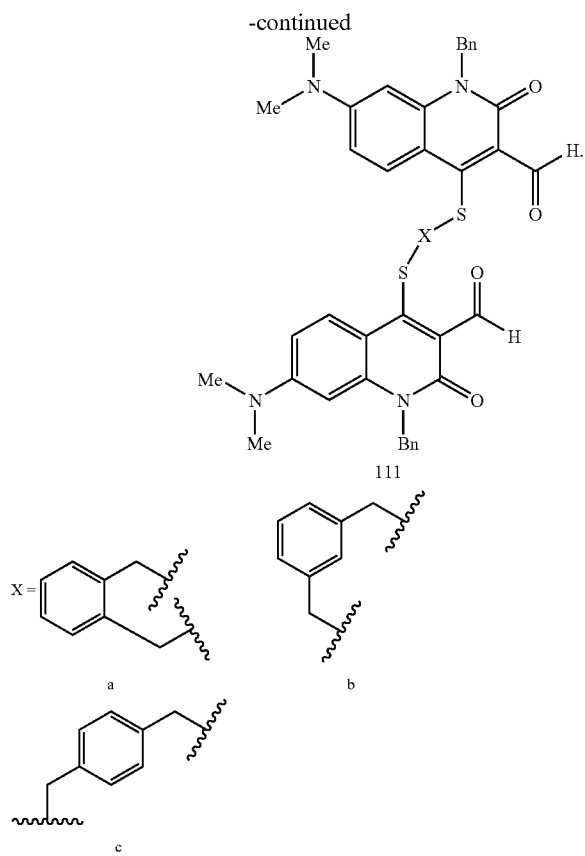

a b c

Generally, the dimeric sensors were not as soluble as the monomeric derivatives, so binding studies were performed in 1:1 methanol:buffer (10 mM HEPES, pH=7.4). Water solubilizing groups, such as polyethylene groups, can be provided on the quinolone core in a straightforward synthetic manner. Binding constants and maximum fluorescence changes ($I_{sat}/I_0$) are provided in Table 4 for a few representative guests.

TABLE 4

Dithiol-linked lysine sensor binding constants and fluorescent changes.

| Sensor | Butyl amine | | Diaminopropane | | Lysine | |
|---|---|---|---|---|---|---|
| | $K_a$ (M$^{-1}$) | $I_{sat}/I_0$ | $K_a$ (M$^{-1}$) | $I_{sat}/I_0$ | $K_a$ (M$^{-1}$) | $I_{sat}/I_0$ |
| IIIa | 130 | 13 | 330 | 6.5 | 780 | 14 |
| IIIb | 93 | 20 | 820 | 14 | 540 | 29 |
| IIIc | 160 | 12 | 590 | 8.3 | 410 | 15 |

Satisfactory results were obtained. The three different linker geometries provide selectivity for guests of different sizes. The short sensor 111a binds best to diaminopropane. In contrast, it binds lysine with an affinity similar to the monoamine. Similarly, the meta-linked sensor 111b binds lysine an order of magnitude better than the mono-amine or the diaminopropane. These data suggest that it should be possible to make very selective sensors for lysine and other diamine analytes by the proper choice of linker in a bis-quinolone sensor.

Biological Evaluation:

As described above, selective sensors for various amines can be prepared and tested in cells. Although completely selective fluorescent sensors have not been achieved, initial testing demonstrates a proof of concept. Compound 112 (Scheme 8 below) is a non-selective sensor with good fluorescence properties and is emissive even when bound to dopamine.

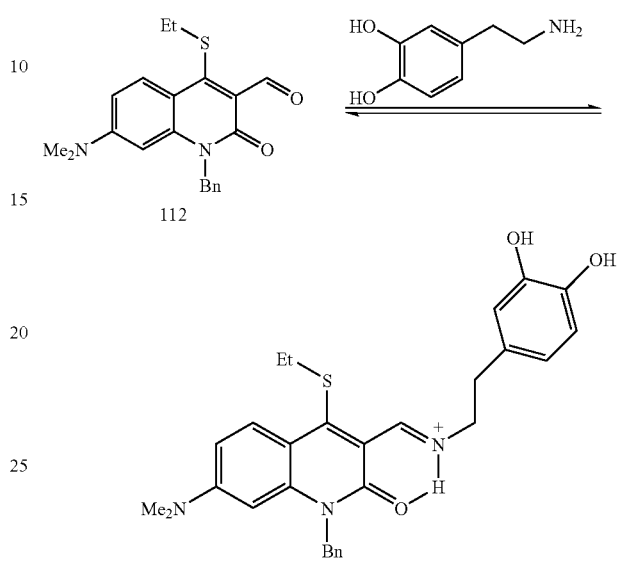

Scheme 8. A non-selective amine sensor.

Figure 13:
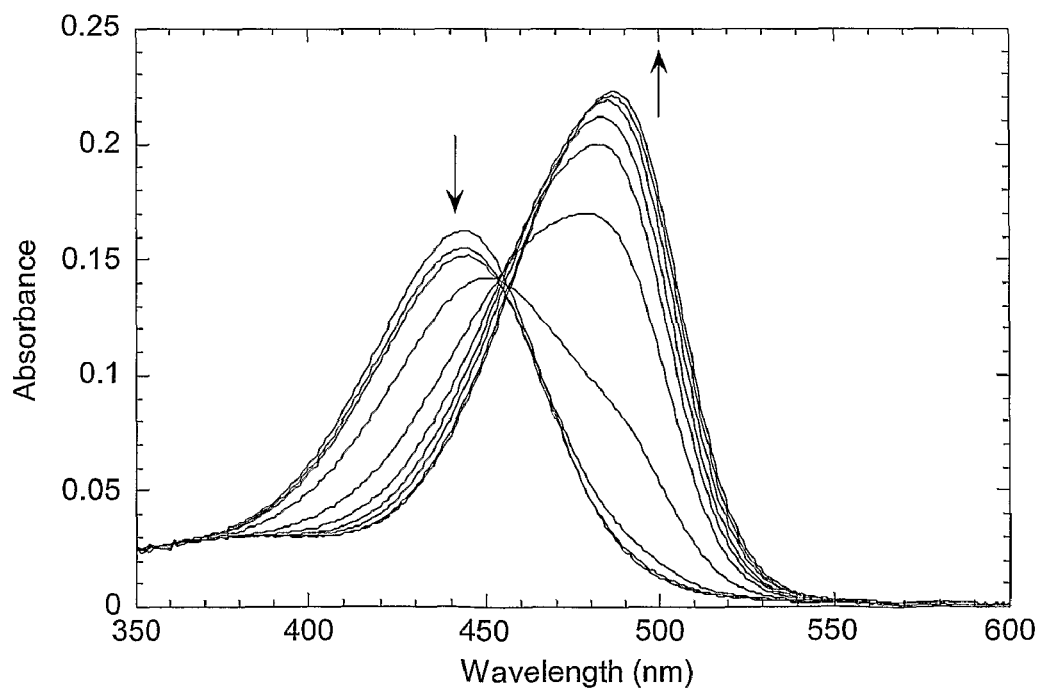
FIG. 13 illustrates the UV/vis response of compound 112 to binding amines.

Compound 112 has the typical UV/vis response to binding amines (FIG. 13) and gives a 7 fold increase in fluorescence when titrated with dopamine. The binding constant for dopamine ($K_a$=180 M$^{-1}$) is similar to that for the binding to most primary amines, accordingly compound 112 was not expected to be a significantly selective sensor for these specific analytes.

Several sets of chromaffin cells (which contain norepinephrine) were freshly prepared on coverslips and various concentrations of 112 in media were added. The optimal sensor concentration was found to be 0.5 μM with 15 minutes of equilibration time. Using confocal microscopy it can be seen that the cells are selectively stained by the sensor. The punctate staining (appearance of bright spots) is indicative of sensor in the vesicles. The nuclei are clearly visible as dark regions. The sensor can obviously enter the nucleus, but lacking high concentrations of amine, do not stain well. These results are surprisingly good for a non-selective sensor. Given that the sensor should bind equally well to all amines, it is likely that that the sensor is actively accumulating in the vesicles.

Sensor 112 is a neutral membrane permeable probe, but the catecholamine adduct is completely protonated in the acidic interior (pH=5.5) and cannot leave the vesicle. This selective membrane permeability combined with the unusually high concentration of catecholamine in the vesicle (1 M) causes the sensor to accumulate in the vesicle. Thus, the sensor is much more selective than its native affinity for amines would predict. There is obviously some cytosolic fluorescence from sensor bound to amines in the cytosol. However, given these excellent results from the non-selective sensor, other compounds described herein should perform as selective sensors very little background fluorescence.

It should be noted that acridine orange is commonly used to visualize synaptic vesicles because, as a weakly basic amine, it accumulates in acidic compartments via a similar mechanism. However, acridine orange accumulates in all acidic compartments (including endosomes, etc.). Sensor 112 is preferable because it stains only acidic compartments which contain a high concentration of amines (neurotransmitters).

Because it is possible to separate chromaffin cells into populations which contain epinephrine and norepinephrine, these cells were used to test sensor 76.

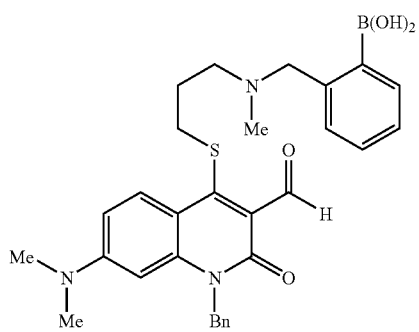

The cells containing norepinephrine (which binds to 76) stained brightly, while the cells containing epinephrine (which does not bind 76) did not stain well under identical conditions. These data indicate that sensors such as 76 will make excellent cellular norepinephrine and dopamine sensors.

These preliminary data demonstrate several important points. The probes are highly fluorescent and require very low concentrations to properly stain the cell. The probes are cell permeable, and do not adversely effect cell viability at the concentrations necessary for staining. The excitation spectra of the probes are within the constraints of the Ar laser (488 nm) pumped confocal microscopes. The probes have an unanticipated ability to accumulate in vesicles. This sensor appears to be the first example of a small-molecule (not protein based) fluorescent sensor that senses an organic analyte in a live cell.

Example 8

Synthesis of Compound 118

Scheme 9 illustrates the preparation of fluorescent sensor 118. The chloride of compound 68 was substituted with a methyl group and the boronic acid was added in a standard fashion. This method of attaching the binding group requires more steps than other methods, but the connection may prove to be more stable in the cell.

Scheme 9. Synthesis of Compound 118.

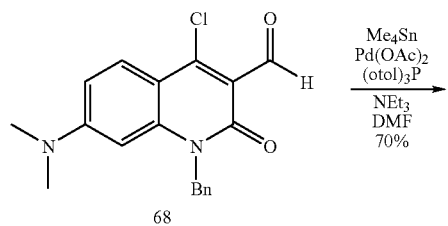

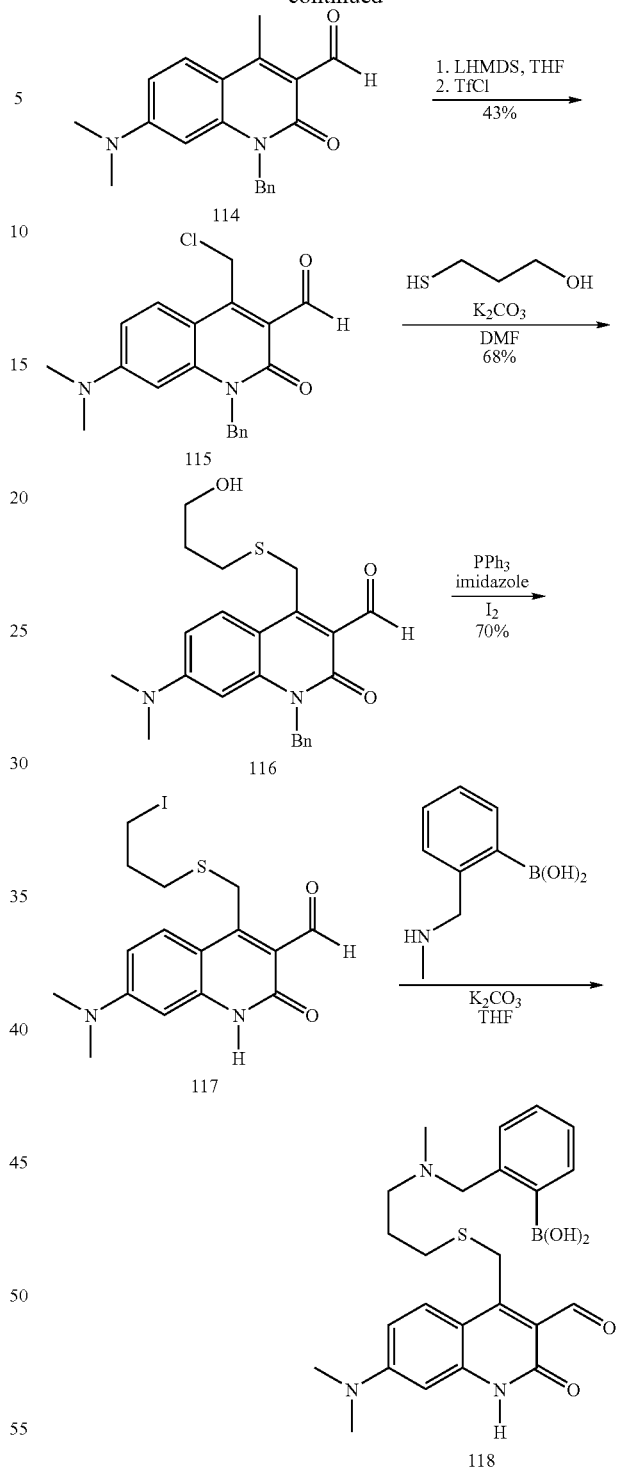

Example 9

Synthesis of Compounds 122 and 123

A phenyl linker has been employed in place of an alkyl linker. This linker is substantially more rigid than the alkyl groups and gives greater flexibility in the type and position of linkage. Compound 68 was coupled with the commercially available boronic acid to give 120. This compound was chlorinated and alkylated to give the boronic acid sensor 122 which had similar binding/fluorescence properties to the alkyl linked compounds.

The substituent on the quinolone nitrogen can also be varied. For example, a series of compounds with a water solubilizing group on that nitrogen have been prepared, such as compound 123. The related derivatives of the formulas of the invention can also be prepared.

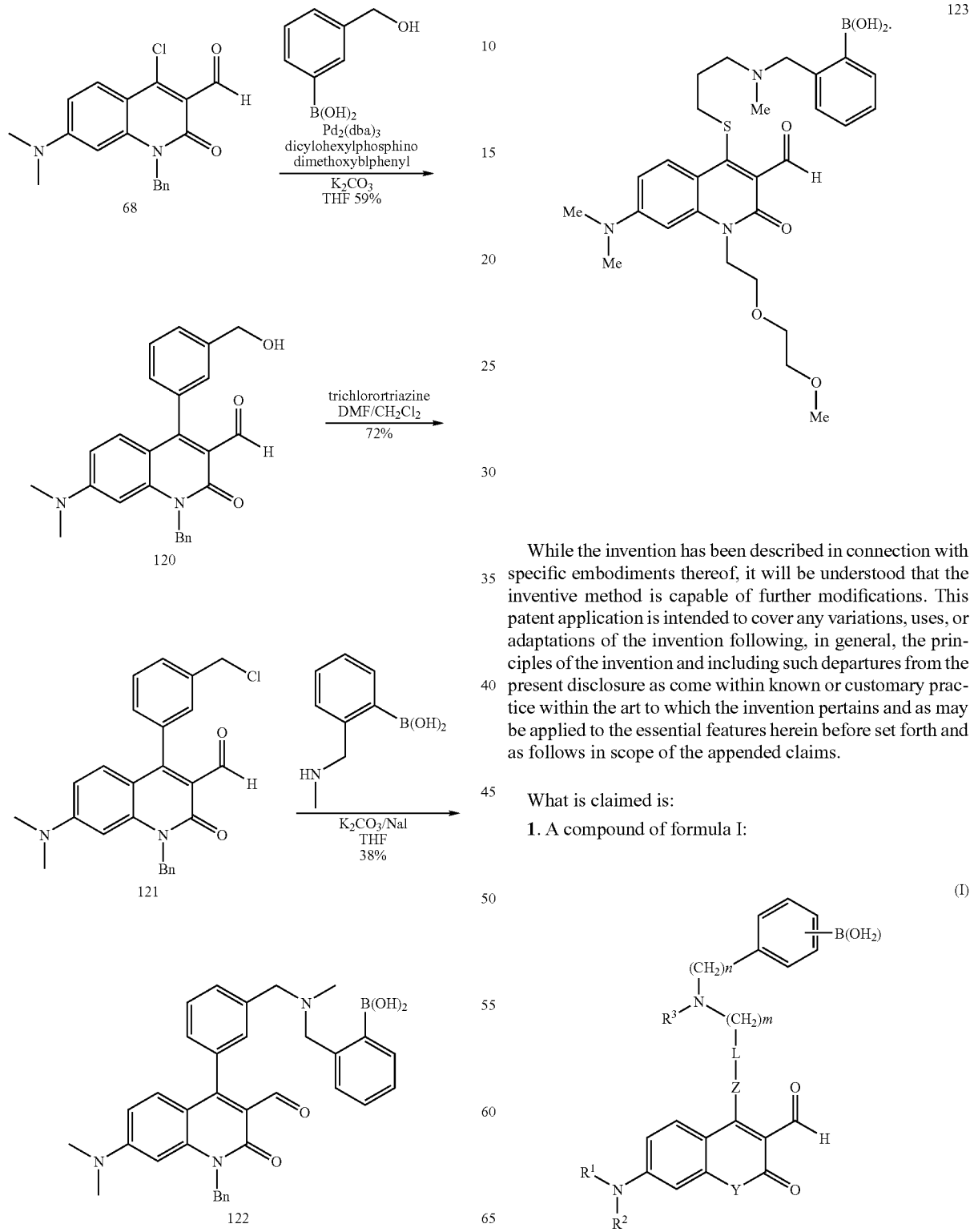

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A compound of formula I:

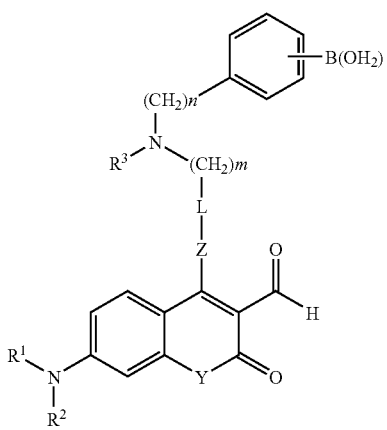

wherein
R[1], R[2], and R[3] are each independently hydrogen, alkyl, aryl, or cycloalkyl; or
R[1] and R[2] together with the nitrogen to which they are attached form a heterocycle with four to six atoms in the ring;
Y is O or N—R wherein R is hydrogen, alkyl, aryl, or cycloalkyl;
Z is —$CH_2$— or a direct bond;
L is O, S, Ph, or a direct bond;
m is 0 to about 6; and n is 1 to about 5.

2. The compound of claim 1 wherein the compound is a fluorescent sensor.

3. The compound of claim 1 wherein R[1], R[2], and R[3] are each alkyl.

4. The compound of claim 1 wherein Y is O.

5. The compound of claim 1 wherein Y is N—R wherein R is alkyl or benzyl.

6. The compound of claim 5 wherein alkyl is a ($C_5$-$C_{20}$) alkyl, and wherein the alkyl chain is optionally interrupted by 1-10 non-peroxide oxygen atoms.

7. The compound of claim 1 wherein L is O, S, or Ph.

8. The compound of claim 1 wherein L is a direct bond.

9. The compound of claim 1 wherein m is 1, 2, 3, 4, or 5, n is 1 and the boronic acid group is an ortho orientation.

10. The compound of claim 1 wherein the compound of formula I is:

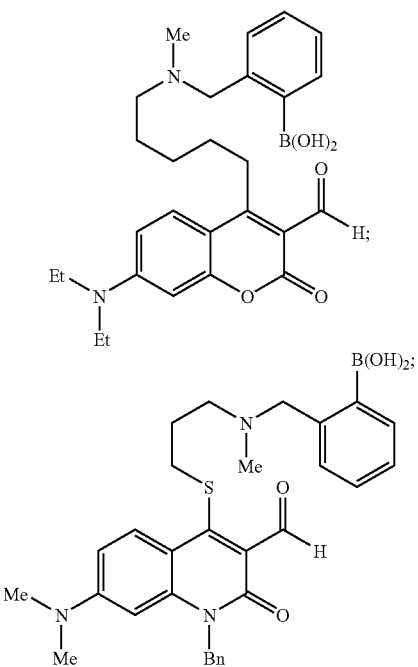

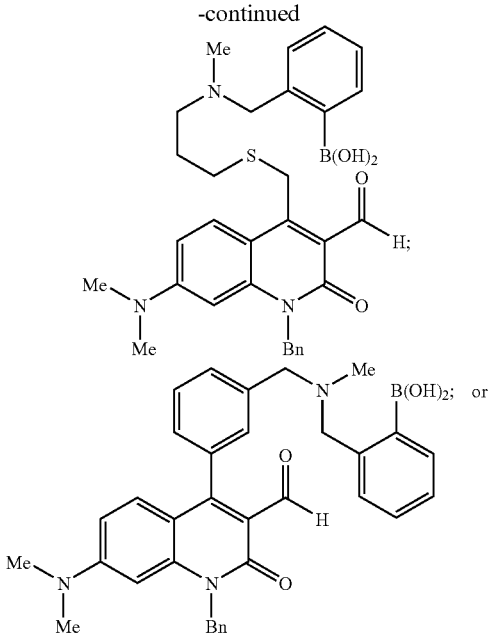

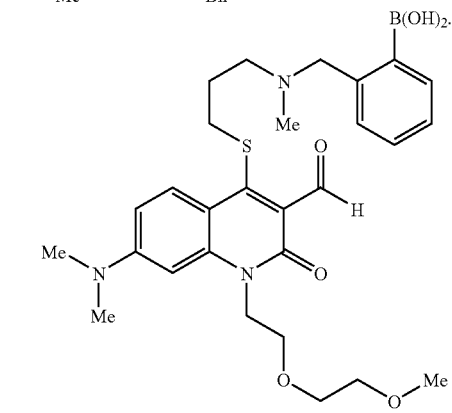

11. A method of detecting an amine-containing analyte in a biological sample comprising contacting the biological sample with the compound of claim 1; and detecting the presence or absence of fluorescence in the sample, wherein the presence of fluorescence indicated the presence of an amine in the sample.

12. The method of claim 11, further comprising measuring the amount of fluorescence in the sample and correlating the amount of fluorescence in the sample with a concentration of the amine in the sample.

* * * * *